United States Patent
Kirchner et al.

(10) Patent No.: US 8,712,518 B2
(45) Date of Patent: Apr. 29, 2014

(54) DETERMINING PHASE-SPECIFIC PARAMETERS OF A PHYSIOLOGICAL VARIABLE

(75) Inventors: Jens Kirchner, Erlangen (DE);
Christian Rockstroh, Nuremberg (DE);
Thomas Kraemer, Nuremberg (DE)

(73) Assignee: Biotronik SE & Co. KG (DE)

( * ) Notice: Subject to any disclaimer, the term of this patent is extended or adjusted under 35 U.S.C. 154(b) by 147 days.

(21) Appl. No.: 13/230,880

(22) Filed: Sep. 13, 2011

(65) Prior Publication Data

US 2012/0078318 A1    Mar. 29, 2012

Related U.S. Application Data

(60) Provisional application No. 61/386,597, filed on Sep. 27, 2010.

(51) Int. Cl.
*A61N 1/365*    (2006.01)

(52) U.S. Cl.
USPC ........ 607/6; 607/17; 607/20; 607/22; 607/62; 600/513

(58) Field of Classification Search
None
See application file for complete search history.

(56) References Cited

U.S. PATENT DOCUMENTS 6,128,534 A * 10/2000 Park et al. ............... 607/17
6,245,021 B1    6/2001 Stampfer

FOREIGN PATENT DOCUMENTS

WO    WO 98/46128 A1    10/1998

OTHER PUBLICATIONS

Da Silva, Lemos M. et al., "Altered cardiovascular responses to chronic angiotensin II infusion in aged rats", *Regulatory Peptides*, Elsevier Science BV, NL, Bd. 132, Nr. 1-3, Dec. 15, 2005, pp. 67-73 (XP027689035).

* cited by examiner

*Primary Examiner* — Kennedy Schaetzle
(74) *Attorney, Agent, or Firm* — Craig A. Fieschko, Esq.; DeWitt Ross & Stevens S.C.

(57) ABSTRACT

The invention relates to methods and systems for determining phase-specific parameters of a physiological variable, and a related computer program and a related machine-readable storage medium, which are usable in particular to determine parameters of physiological variables that are subject to circadian variation. To this end, phase-specific parameters of a physiological variable $X(t)$ are determined by calculating, at least for a portion of values x lying in a specifiable time period, a mean $g(x|\tau)$ in each case of values $X(t+\tau)$ for which $X(t)=x$ applies for their predecessors, $\tau$ describing a time interval, and determining the phase-specific parameters by evaluating the mean $g(x|\tau)$.

19 Claims, 17 Drawing Sheets

DETERMINING PHASE-SPECIFIC PARAMETERS OF A PHYSIOLOGICAL VARIABLE

CROSS-REFERENCE TO RELATED APPLICATIONS

This patent application claims the benefit of U.S. Provisional Patent Application No. 61/386,597, filed on Sep. 27, 2010, which is hereby incorporated by reference in its entirety.

FIELD OF THE INVENTION

The invention relates to a method and a system for determining phase-specific parameters of a physiological variable, and a related computer program and a related machine-readable storage medium, which are usable in particular for determining parameters of physiological variables that are subject to circadian variation.

BACKGROUND OF THE INVENTION

Circadian variation, i.e. the periodic fluctuation of a physiological variable due to a patient's daily rhythm, is a phenomenon that affects data measured in human beings over long time periods, in particular over a period of 24 hours; see, e.g., FIG. 1. Circadian variation reflects the daily activity of the patient as compared to the nocturnal resting state, and thereby also indirectly reflects the capacity of the cardiovascular system. This suggests that parameters that describe circadian variation in a quantitative manner are potential indicators of the development or worsening of cardiac disease.

It has similarly been determined that the periods during which a patient is sleeping or awake are markedly different physiological situations for the cardiovascular system. These time periods should therefore be handled separately when performing data analysis, in particular when calculating relevant diagnostic parameters. To this end, the boundaries between day and night must be identified in advance.

The invention described below involves methods for determining the means (averages) of physiological variables that are subject to day and night periods of the circadian variation, in particular heart rate. These methods can be used to calculate diagnostically valuable quantities for diagnosing and monitoring cardiac diseases, and to delineate the time intervals in which the patient is awake or sleeping, to thereby select data segments that are suitable for use in other data analysis methods. Furthermore, medical devices, and in particular implantable devices (e.g., cardiac pacemakers, implantable cardioverters/defibrillators, implantable devices for patient monitoring, and the like) equipped with this algorithm can tailor their functions in a patient-specific manner to the different demands in the day phase or the night phase, and thereby further improve the patient's quality of life.

From the prior art it is known to determine the respective day and night means of physiological variables at fixed points in time, for short measuring times. Day and night is phases are thereby defined on the basis of fixed time boundaries, or patient-defined protocols are used. Determining the means at fixed points in time has three disadvantages:

1. They are negatively affected by individual/temporary deviations of the rhythm that has set in. For example, measurements of the nocturnal heart rate at 3:00 a.m. are influenced by whether the particular patient has just fallen asleep, is now in a phase of deep sleep, will wake up soon, or is going to the bathroom.
2. They are based on a short measuring time. As a result, they are more susceptible to interferences of the kind described in the example above.
3. By definition, they do not provide a quantification of the circadian variation in the sense of determining sleeping times and waking times.

As an extreme example, the heart rate is measured at 3:00 a.m. when the patient wakes up briefly, and in the afternoon when the patient takes an afternoon nap. Using this approach, complete inactivity of the patient would be detected since there is little difference between the diurnal heart rate and the nocturnal heart rate. A similar problem arises, for example, when data is only analyzed in a time period defined as the nocturnal phase. This procedure discards a portion of the data that are actually available, and/or runs the risk of also integrating data from the waking phase.

The use of patient-defined protocols which rely on the patient to define diurnal, nocturnal, or intermediate periods is disadvantageous for the following reasons:

1. They are unreliable because they are dependent on the thoroughness and mental acuity of the patient.
2. They pose an imposition on the patient.

SUMMARY OF THE INVENTION

The invention provides a method and a system for determining phase-specific parameters of a physiological variable, and a related computer program and a related machine-readable storage medium, which avoid the disadvantages of the conventional solutions and, in particular, make it possible to quantify the circadian variation without preconceptions regarding (for example) the number or location of the phases of the circadian variation.

A particular advantage of the inventive method is that parameters of a physiological variable $X(t)$, such as heart rate, respiration, (bio)chemical signals (e.g. fluctuations in the concentration of biomarkers) or the like, can be determined for various phases of the physiological variable $X(t)$ without prior knowledge (or with inadequate knowledge) of the number and/or boundaries of the phases of the variable $X(t)$. This can be achieved by defining a function $g(x|\tau)$ of mean target states depending on a starting state that preceded it by $\tau$: $g(x|\tau)=<X(t+\tau)>_{X(t)=x}$. In this manner, the temporal mean is calculated of all values $X(t+\tau)$, the predecessors $X(t)$ of which had the value x. Since the physiological variable $X(t)$ can also be heart rate, for example, the variable t will also be used in the following to refer to time, measured in seconds, as well as the beat number. The same applies for the delay time $\tau$ in seconds, which can also be interpreted as an interval in beats. In general, t describes an instant or an event of the physiological variable $X(t)$ such as a heartbeat or the number of an event, and $\tau$ describes a time period or a number of events. By evaluating the function $g(x|\tau)$, parameters can be obtained that are related to various phases of the variable $X(t)$, in particular being related to the circadian variation or other physiologically characterized time periods. In a preferred version of the method, further secondary parameters are determined from the sensor signal $X(t)$ itself, or in combination with further measured variables.

The parameters obtained in this manner can be used, for example, as indicators of cardiac diseases such as cardiac insufficiency, or as indicators of sleep disorders. The parameters obtained in this manner can also be used to identify data segments of the stated sensor signal $X(t)$ or another measured variable for further data processing.

In a preferred version of the invention, the determination of phase-specific parameters includes the determination of at least one phase-specific mean $\xi$, which assumes the variable X(t) in a certain phase, or includes the determination of boundaries and/or the length of phases. As a result, parameters for quantifying the circadian variation are obtained as a means for diagnosing and monitoring cardiac diseases. In particular, the parameters obtained using the inventive method can also be used to quantify the sleep behavior of a patient, on the basis of which sleep disorders can be diagnosed and monitored.

In a preferred version of the invention, the values of the heart rate are evaluated. Examples of parameters determined therefrom are:

Diurnal mean $\xi_1$ (the diurnal phase)
Nocturnal mean $\xi_2$ (the nocturnal phase)
The difference ($\xi_2-\xi_1$) between diurnal mean and nocturnal mean
The number of beats in the nocturnal phase, i.e. the number of beats above a threshold value, for example, #{X(t)|X(t)>$\xi_2-\frac{1}{4}\cdot(\xi_2-\xi_1)$}
Number of beats in the diurnal phase
Length of the nocturnal phase
Length of the diurnal phase It is furthermore advantageous to classify the values of the variable X(t) by assigning the values of X(t) to at least a portion of the phases. This assignment can be based on the means $\xi$ of the individual phases, for example, by using one or more of the means to define one or more threshold values, and the values X(t) are assigned to a phase depending on their relation to the threshold value(s).

In another preferred version of the invention, the location of the phases, i.e. the boundaries and/or lengths of the phases, is determined by evaluating the classified values of X(t). The determination of the location of the phases can include, for example, an optimization. As an example, the boundaries of a phase can be determined by maximizing the number of values assigned (e.g. via classification) to a first class within the first phase, and maximizing the number of values assigned to a second phase before and after the first phase by varying the phase boundaries. In another preferred version, the boundaries of a phase are determined by examining time intervals of a specified length for an observation period (of, for example, 24 hours) to determine whether the number of values X(t) included in a time interval that were assigned to a first phase have a certain specifiable relationship to the number of values X(t) included in this time interval that were assigned to a second (or third) phase, and by assigning the time interval to a phase on the basis of this relationship. In this case of heart rate X(t), which is used as an example, the first phase and the second phase can respectively be the diurnal phase and the nocturnal phase, and the beats can be classified as diurnal beats or nocturnal beats in a manner described further below.

A particular advantage of the invention is that, in addition to enabling the circadian variation to be determined, also makes it possible to identify smaller structures of physiological variables such as deep-sleep phases, REM sleep, an afternoon nap, or times of high stress. This is achieved by performing a recursive evaluation of the function g(x|τ) of the mean target states. In a first step, the inventive method is used to determine, for example, boundaries and length of a first quantity of phases of the variable X(t) by defining and evaluating the function g(x|τ) for a first specified time period, for example, a day. In a second step, the method is applied to one or, in parallel, several phases determined in the first step, with a new function g(x|τ) being defined for each of the phases now being investigated. Preferably, the duration (or number) τ is adapted to the length of the investigated phases and/or the events to be investigated, such as deep sleep, REM-sleep phases, or the like. Preferably τ is selected such that τ is less than the duration of the events to be investigated.

In a further preferred version of the invention, the function g(x|τ) is approximated by a piecewise linear function $y_1(x)$. Preferably, the function $y_1(x)$ covers ranges in which the function $y_1(x)$ has a constant shape. The ranges of constant shape are connected by ranges in which the function $y_1(x)$ has a linearly increasing or decreasing shape. It has proven advantageous to define the function $y_1(x)$ as follows:

$$y_1(x) = \begin{cases} \xi_1 & \text{if } x < \xi_1 + dx \\ x & \text{if } \xi_1 + dx < x < \xi_2 - dx \\ \xi_2 & \text{if } \xi_2 - dx < x, \end{cases}$$

with free parameters dx, $\xi_1$ and $\xi_2$. Preferably, dx is chosen such that dx=0. However, dx>0 can be advantageous to better adapt the function y(x) to the shape of the function g(x|τ).

In a further preferred version of the invention, the function g(x|τ) is approximated by a sigmoidal function $y_s(x)$. A person skilled in the art can identify further fit functions for g(x|τ).

To avoid artifacts which are caused, for example, by values of the function g(x|τ) that are based on a smaller foundation of data, it has proven advantageous to weight the $\chi^2$ value. In a preferred version, the $\chi^2$ value is weighted depending on the frequency distribution P(x)=#{X(t)=x}/#{X(t)} of the values of X(t). In that function and in the following, "#" stands for the number of elements in the associated quantities. It has also proven advantageous to use weighting to prevent dominance by large values of g(x|τ). This can be achieved, for example, by selecting the weighting to be smaller than the frequency P(x), and preferably to be constant, above a certain frequency P(x). It can also prove advantageous to calculate $\chi^2$ only for a limited domain of g(x|τ).

A system according to the invention includes at least one chip and/or processor, and is designed such that a method for determining phase-specific parameters of a physiological variable X(t) can be implemented, wherein for at least a portion of values x lying in a specifiable time period, a mean g(x|τ) is calculated in each case of values X(t+τ) for which X(t)=x applies for their predecessors, τ describing a time interval, and then determining the phase-specific parameters by evaluating the mean g(x|τ).

In a preferred version of the invention, the system includes a sensor for measuring a physiological variable X(t) such as heart rate. In addition, the system preferably includes a data evaluation unit which can be implemented as part of an implant in the body of a patient, or as an external device. The implant can be, for example, a cardiac pacemaker, a defibrillator (e.g., an Intra Cardiac Defibrillator or ICD), or a device for patient monitoring, for example, a decompensation predictor (e.g., a Worsening of Heart Failure Predictor or WHFP). Likewise, the device for patient monitoring can be realized entirely as an external device, or it can be composed of one or more implantable components and one or more external components which are interconnected constantly or temporarily in a suitable manner, for example, electrically or via a magnet coil or telemetry.

The data evaluation preferably includes the determination of the function of the mean target states $$g(x|\tau) = \langle X(t+\tau) \rangle_{X(t)=x}$$

depending on the starting state x which is earlier by τ, that is, the temporal mean of all values X(t+τ), the predecessors X(t) of which (the cycle that took place τ beats earlier) had the value x. Proceeding from the data obtained in this manner, parameters can be determined that are proportional to the circadian variation or other physiologically characterized time periods. Optionally, further secondary parameters can also be determined, either from the sensor signal X(t) itself, or in combination with one or more measured variables.

The data evaluation to determine the function g(x|τ) can be performed continually, i.e. it can be updated by progressively registering the sensor signal X(t), or after the sensor signal X(t) has been registered, by evaluating the entire quantity of data that were registered. The advantage of continual adaptation is that relatively small computing resources are required to perform the updating, while very large quantities of data must be evaluated, for instance, when g(x|τ) is determined after the measurement procedure has been completed.

The invention makes it possible to reduce the quantity of data to be transmitted, in particular when the physiological data are registered using an implant, transmitted using telemetry, and processed in an external device. Calculating the function g(x|τ) in the implant reduces the number of cycles, for example, of the heart rate, to be stored in the implant to τ cycles. In addition, its g value, the value range, and the number of data points that have contributed thus far to the g value must be stored for each bin. For example, when the measuring range is covered using 1000 bins, and the delay time is τ=1000, the implant should be capable of storing 4000 data points. Of these (provided that the bin boundaries are fixed), only the 1000 data points of the plot of g are transmitted to an external device. Compared to a 24-hour measurement in which (typically) approximately 100,000 data points are registered, this represents a substantial reduction in the quantity of data to be stored and transmitted.

The parameters and/or information, e.g., on the sleep behavior of a patient, that are obtained using the invention are utilized in a preferred version of the invention to adapt functions of the system, in particular of a cardiac pacemaker, an ICD, and/or cardiac monitor (WHF predictor), in an individualized manner and preferably automatically.

A computer program for determining phase-specific parameters of a physiological variable X(t) makes it possible, once it has been loaded in the memory of a data processing device, for the data processing device to determine phase-specific parameters wherein for at least a portion of values x lying in a specifiable time period, a mean g(x|τ) is calculated in each case of values X(t+τ) for which X(t)=x applies for their predecessors, τ describing a time interval, and the phase-specific parameters are then determined by evaluating the mean g(x|τ).

In a further preferred version of the invention, the computer program is modular, wherein individual modules are installed on various data processing devices.

Additional computer programs can also be provided to implement further method steps or method sequences described below.

Computer programs of this type can be provided for downloading (for a fee or free of charge, or in a freely accessible or password-protected manner) in a data network or communication network. The computer programs provided in this manner can then be utilized by a method by downloading a computer program from an electronic data network is (such as the Internet) onto a data processing device that is connected to the data network.

A machine-readable storage medium can be provided to implement the inventive method for determining phase-specific parameters of a physiological variable X(t), on which a program is stored that makes it possible, once it has been loaded in the memory of a data processing device, for the data processing device to determine phase-specific parameters, wherein for at least a portion of values x lying in a specifiable time period, a mean g(x|τ) is calculated in each case of values X(t+τ) for which X(t)=x applies for their predecessors, τ describing a time interval, and the phase-specific parameters are then determined by evaluating the mean g(x|τ).

The invention provides an efficient method for determining phase-specific parameters of a physiological variable X(t) while avoiding the above-stated disadvantages of the prior art in the sense that it is not negatively affected by individual or discretely occurring fluctuations in the typical circadian rhythm. This is due to the fact that it makes no assumptions about the number, location and (at least as far as is possible) the length of the waking phase and the sleeping phase. Furthermore, it eliminates the use of patient protocols.

In tests it has been furthermore shown that the invention functions with patients who are dependent on pacemakers, and with subjects who do not have an implant. The presence of periods without an intrinsic rhythm therefore does not negatively affect the method.

A further advantage of the method is that it can utilize the sensors that are already present in implants, and is not dependent on the integration of an additional measuring system. In particular, it is not necessary to use acceleration sensors or motion sensors.

The invention could be integrated in a decompensation predictor, as a data processing means for analytical methods that are already used or other analytical methods that will be implemented, or with the above-described parameters, which are derived from the circadian variation, as indicators of a worsening/development of CHF.

In addition to cardiac diseases, it is also possible to detect and monitor various sleep disorders, in particular sleep apnea.

The invention makes it possible to determine means of a physiological variable, in particular heart rate, as well as, for example, respiration, (bio)chemical signals (e.g. fluctuations in the concentration of biomarkers), etc., during a plurality of phases under physiologically different conditions, in particular during sleeping phases and waking phases. The number of these phases and their temporal limits are not known, or are not known exactly.

The knowledge of these means, and possibly their number, can be used to derive:

Boundaries of the associated time periods;
Parameters for quantifying the circadian variation as a means for diagnosing and monitoring cardiac diseases;
Parameters for quantifying a patient's sleep behavior as a means for diagnosing and monitoring sleep disorders.

To this end, at least a portion of the data volume that is obtained by measuring physiological variables X(t) is evaluated, wherein the start and/or end points of the time periods, such as the location and duration of the sleeping and waking phases, are not known. Preferably, the entire data volume is used for the evaluation.

Simple examples of parameters that are derived in this manner are the difference between the diurnal heart rate and the nocturnal heart rate, which is reduced in patients with cardiac insufficiency. The number and length of deep-sleep phases and REM-sleep phases provide information about the patient's sleeping rhythm, thereby making it possible, for example, to diagnose sleep apnea. The parameters that are derived are therefore used as indicators of the patient's health status.

When the exact boundaries of the analyzed time periods are known, e.g., the boundaries between sleeping and being awake, then suitable data segments can be identified for the is further data analysis using other methods. For example, it is therefore possible to limit the signal analysis to the sleeping phase.

Furthermore, the results of the algorithm presented above can be used to better adapt the behavior of the implant to the sleeping rhythm of the implant wearer.

BRIEF DESCRIPTION OF THE DRAWINGS

The invention is explained below using several versions as examples, with reference to the FIGS. of the drawings. They show.

DETAILED DESCRIPTION OF EXEMPLARY VERSIONS OF THE INVENTION

In the exemplary versions of the invention described below, heart rate X(t) is evaluated as an example. Instead of heart rate X(t), it is also possible to evaluate any other (physiological) variable, such as respiration or (bio)chemical signals (e.g. fluctuations in concentration of biomarkers), which is characterized by two or more phases.

Determination of the Means of the Diurnal Phase and the Nocturnal Phase

First, the frequency distribution of the measurement signal is determined:

$$P(x) = \#\{X(t)=x\}/\#\{X(t)\}.$$

From this point forward, the discussion will focus on pairs of data points {X(t); X(t+'r)} having a fixed interval τ which is, for example, 1000 cardiac cycles.

The function g(x|τ) of the mean target states is defined depending on the starting state x=X(t):

$$g(x|\tau) = \langle X(t+\tau) \rangle_{X(t)=x}$$

Figure 1:
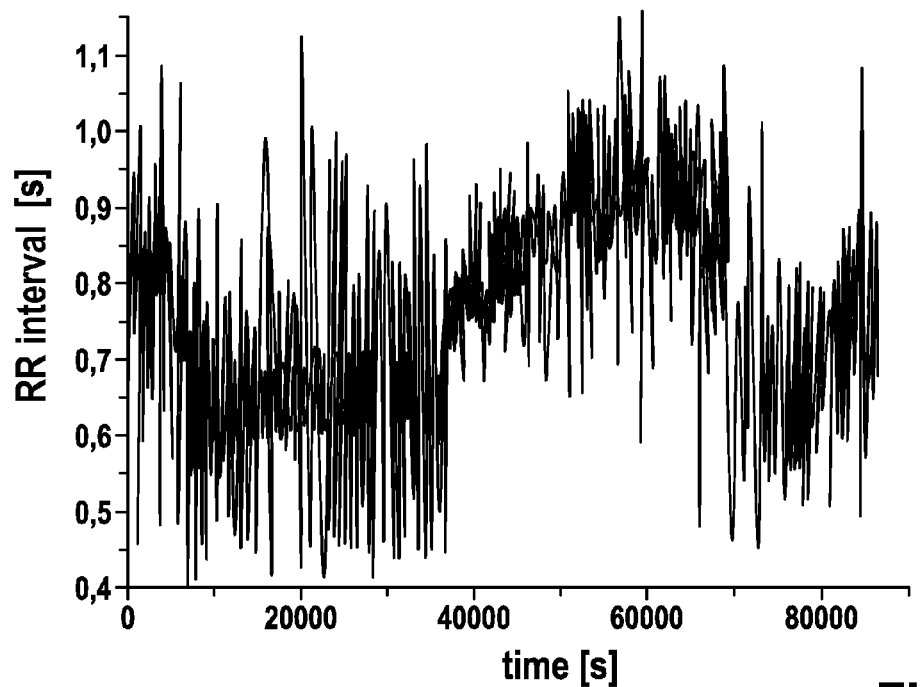
FIG. 1 an example of a time series of RR intervals over 24 hours.
Figure 2:
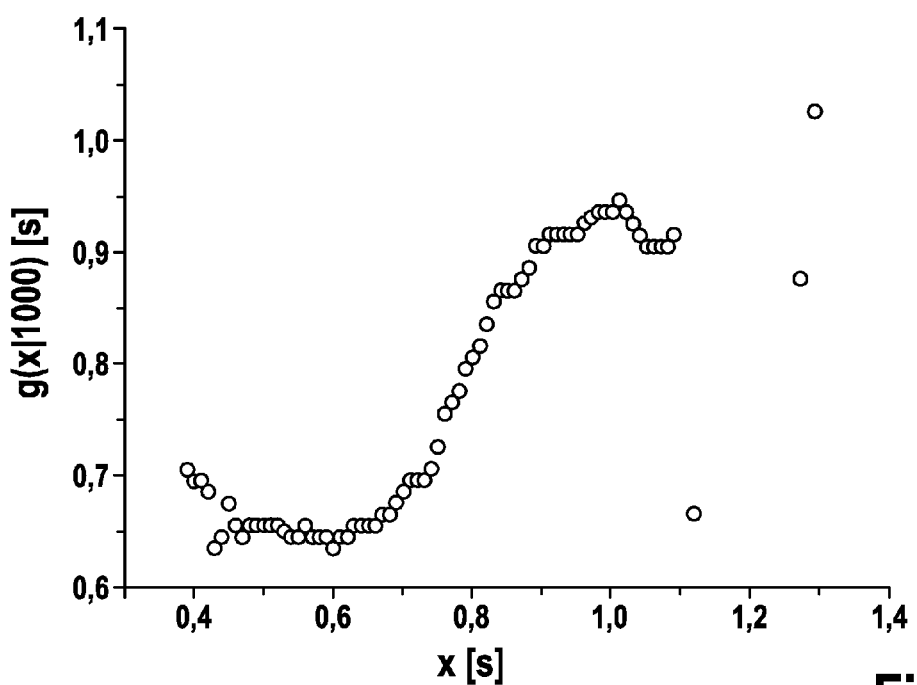
FIG. 2 the function g(x|τ) of the mean target states, which is derived from the time series shown in FIG. 1.

As an example, FIG. 2 shows the function g, which is calculated on the basis of the time series shown in FIG. 1, with time difference τ=1000 beats. FIG. 2 shows the function of the mean target states g(x|τ), which is determined on the basis of the time series shown in FIG. 1 using the above-defined formula. At small RR intervals (x in the range x=0.4 ... 0.6 s), the mean target RR interval is g≈0.65 s. When x is high (x=0.9 ... 1.1 s), the mean target level is g≈0.95 s. Between these two ranges lies an approximately linear transition phase having a slope equal to 1.

The function g indicates the heart rate which is the target, on average, within the time period defined by τ, when the heart rate was previously x. In the case of data that are subject to circadian variation, two distinct plateaus now appear; they have height $\xi_1$ and $\xi_2$, which extend from x=min(x) to x=$\xi_1$ and from x=$\xi_2$ to x=max(x). These two plateaus are connected by a transition region in which the data typically have a slope equal to 1.

For this reason, the following fit function $y_1(x)$ having the two free parameters $\xi_1$ and $\xi_2$ are adapted to the data:

$$y_1(x) = \begin{cases} \xi_1 & \text{if } x < \xi_1, \\ x & \text{if } \xi_1 < x < \xi_2, \\ \xi_2 & \text{if } \xi_2 < x. \end{cases}$$

The $\chi^2$ value is also weighted in a suitable manner depending on the frequency distribution P(x). The following weighting function, for example, has proven advantageous:

$$w(x) = \begin{cases} P(x) & \text{if } P(x) < w_{max} \\ w_{max} & \text{otherwise,} \end{cases}$$

wherein $w_{max}$ is the maximum value of w(x), which is defined, for example, as a portion of the maximum P(x) or depending on the number of x bins. The function w(x) weights rare x values to a lesser extent than the rest, to thereby avoid artifacts by g values based on a smaller foundation of data, while also avoiding an excessive dominance by individual g values by using a uniform distribution for all P(x) above the threshold.

Further possible modifications include limiting the x-range on which $\chi^2$ is calculated, or reducing the interval on which the fit function is y(x)=x, from [$\xi_1$; $\xi_2$] to [$\xi_1$+dx; $\xi_2$−dx].

The optimal fit parameters $\xi_1$ and $\xi_2$ are then the means of the diurnal phase and the nocturnal phase, respectively.

Determination of the Boundaries of the Diurnal Phase and the Nocturnal Phase

The boundaries of the phases can be determined from the means of the diurnal and nocturnal phases using the following steps.

Define a threshold value z, e.g.

$$z = \xi_2 - \frac{1}{4} \cdot (\xi_2 - \xi_1).$$

Map the heart rate signal X(t) onto a symbol series S(t) as follows $$S(t) = \begin{cases} 0 & \text{if } X(t) < z \quad (\text{"diurnal beat"}) \\ 1 & \text{otherwise} \quad (\text{"nocturnal beat"}) \end{cases}$$

Determine the boundaries of a continuous nocturnal phase, for example, as follows:
Optimize the boundaries $T_1$ and $T_2$, thereby ensuring that the number of nocturnal beats in the nocturnal phase and the number of diurnal beats in the two phases before and after the nocturnal phase are maxima, i.e. $\chi(T_1, T_2)$, defined by $$\chi(T_1, T_2) = \chi_1(T_1) + \chi_2(T_1, T_2) + \chi_3(T_2) \text{ with:}$$

$$\chi_1(T_1) = \#\{S(t)=0 | t<T_1\}/\#\{S(t)|t<T_1\}$$

$\chi_2(T_1,T_2) = \#\{S(t)=1 | T_1 < t < T_2\} / \#\{S(t) | T_1 < t < T_2\}$ $\chi_3(T_2) = \#\{S(t)=0 | T_2 < t\} / \#\{S(t) | T_2 < t\}$ is maximized with respect to free parameters $T_1$ and $T_2$; and Use the largest continuous group of "night windows", i.e. windows having a defined width, for example, 5 minutes, in which the number of nocturnal beats is greater than the number of diurnal beats. Other relations of numbers can also be used, which could be used to control the sensitivity of the algorithm and/or the depth of sleep, although the one phase is identified as the sleeping phase. The latter possibility is explained by the fact that, in light of the variability of the heart rate, the frequency of nocturnal beats in one window is associated with the distance of the mean heart rate in this window from the threshold value z. This method can also be used to identify several nocturnal phases in a measurement without specifying their number.

The boundaries $T_1$ and $T_2$ of diurnal and nocturnal phases obtained in this manner can be used, for example, to limit a more extensive data analysis to certain data segments, for example, to the sleeping phase. A procedure of this type is of interest because the physical load that exists in the sleeping phase is comparable among all patients, or because vagotonia is particularly high.

Similar to the definition of z, two threshold values can also be defined, for example, $z_1 = \xi_1 + \frac{1}{4} \cdot (\xi_2 - \xi_1)$ and $z = \xi_2 - \frac{1}{4} \cdot (\xi_2 - \xi_1)$, using which a diurnal range, a nocturnal range, and a transition range situated therebetween can be defined. The range represented by "S" is increased accordingly by one. In addition to means $\xi_2$ and $\xi_1$, measures of dispersion, for example, can also be incorporated into the definition of the threshold values, for example, the variance of the entire time series or the variance as a function of the associated mean, which is calculated in a window.

Derivation of Diagnostically Relevant Parameters

The following parameters provide an indication of the cardiac state of the patient:

Diurnal mean $\xi_1$
Nocturnal mean $\xi_2$
The difference ($\xi_2 - \xi_1$) between diurnal mean and nocturnal mean
The number of beats in the nocturnal phase, i.e. $\#\{X(t) | X(t) > \xi_2 - \frac{1}{4} \cdot (\xi_2 - \xi_1)\}$
Number of beats in the diurnal phase
Length of the nocturnal phase
Length of the diurnal phase The first three are determined directly from the $g(x|\tau)$ plot, and the remainder are determined in combination with the original time series X(t).

Figure 3:
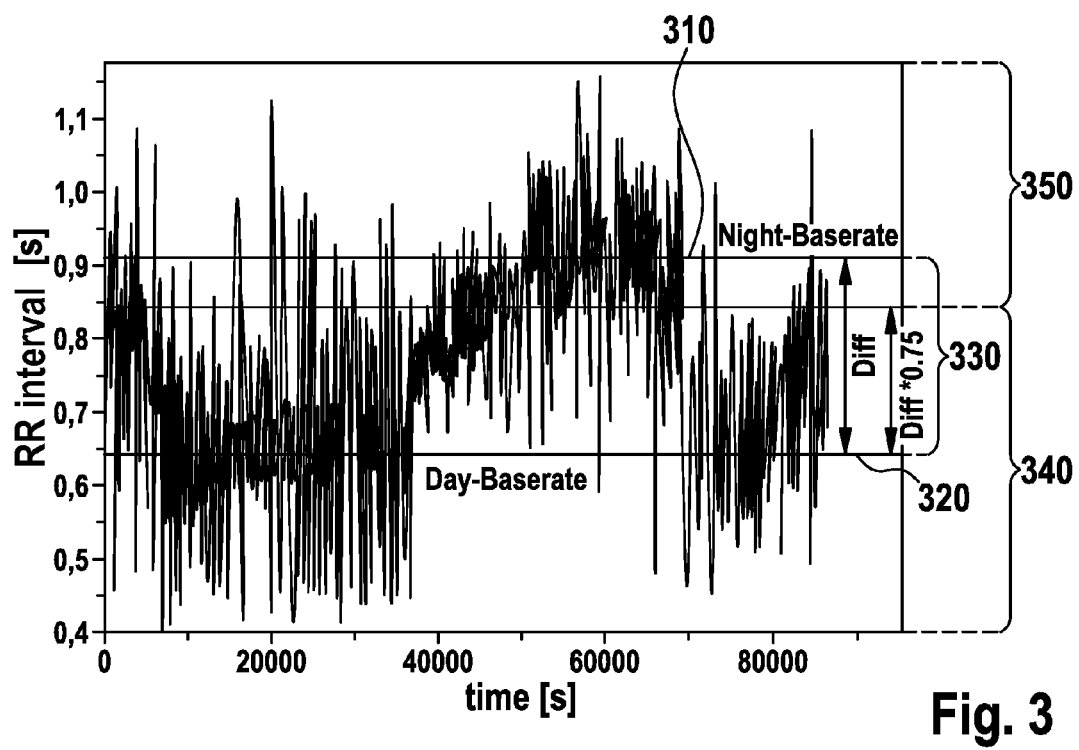
FIG. 3 a representation of the parameters determined from the g(x|τ) plot in the time series X(t) shown in FIG. 1, FIG. 4 a visualization of parameters determined from the g(x|τ) plot (FIG. 2), FIGS. 5-8 the plot of g for four different patients 1 through 4, FIGS. 9-12 comparisons of RR intervals 910, sleeping/waking phases 920 reconstructed according to the invention, and phases according to annotations 930, and FIGS. 13-21 a comparison of the following data from eight subjects:
Panel 1: the plot of g and the line y=x (1310, scale on the left), relative frequency of the RR intervals (1320, scale on the right), and $\xi_1$ and $\xi_2$ (410, 420, as vertical lines)
Panel 2: the time series of RR intervals 910 and $\xi_1$ and $\xi_2$ (310, 320, as horizontal lines)
Panel 3: the time series of RR intervals after smoothing, with window width N=10 beats (at 1330) and N=300 beats (at 1340)
Panel 4: relative frequency distributions 1350, 1360 of smoothed RR interval time series 1330, 1340
Figure 4:
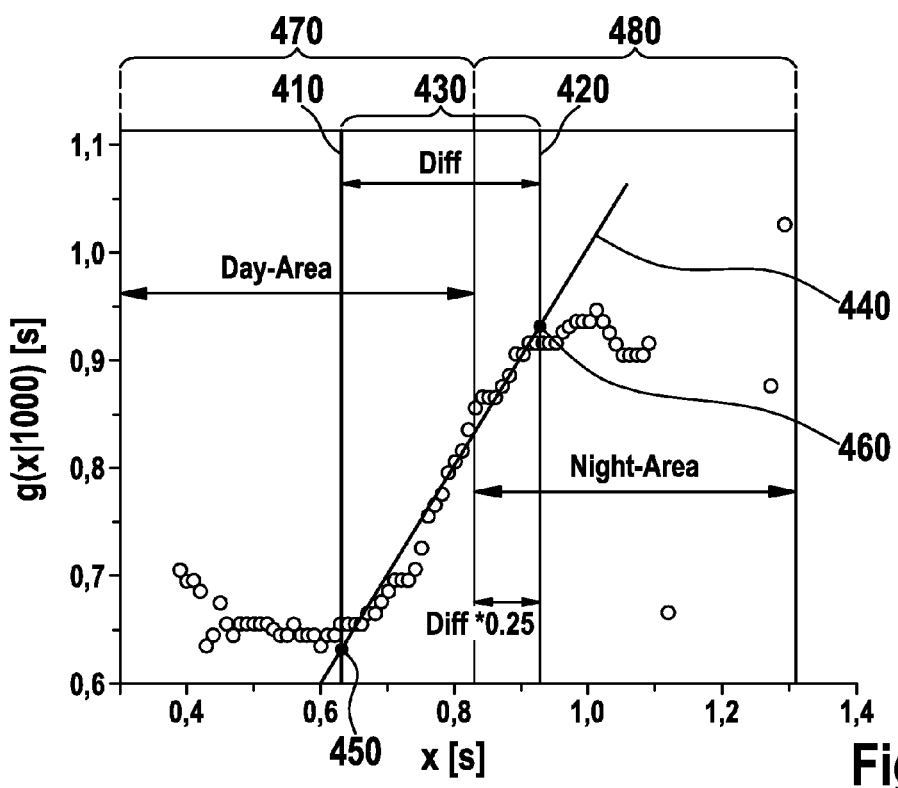
Figure 5:
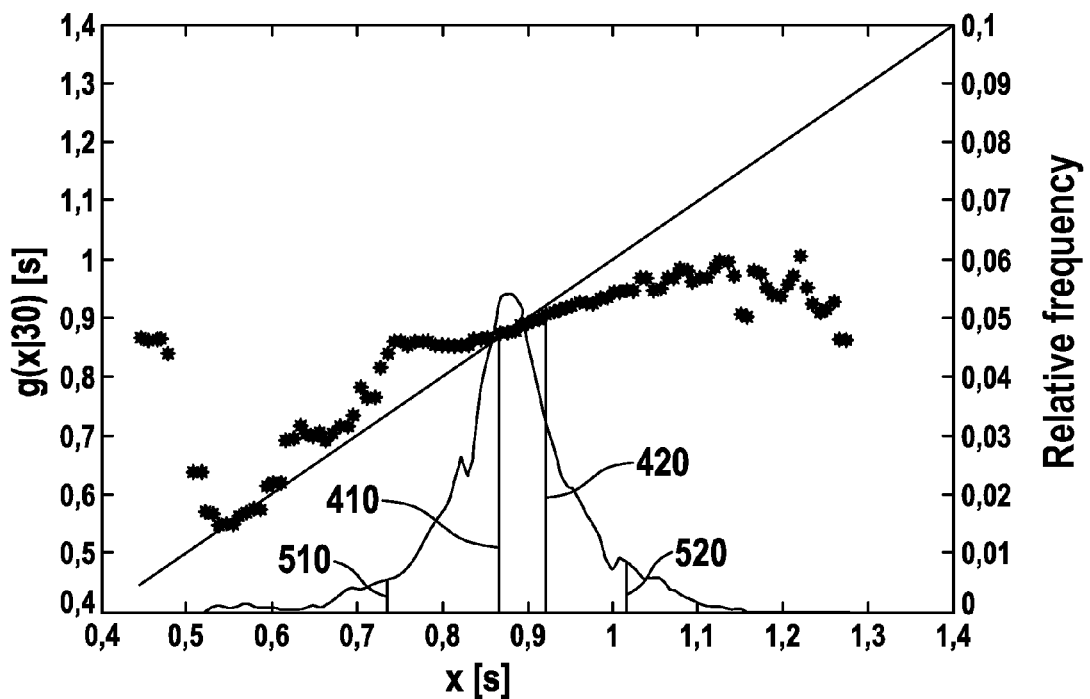
Figure 6:
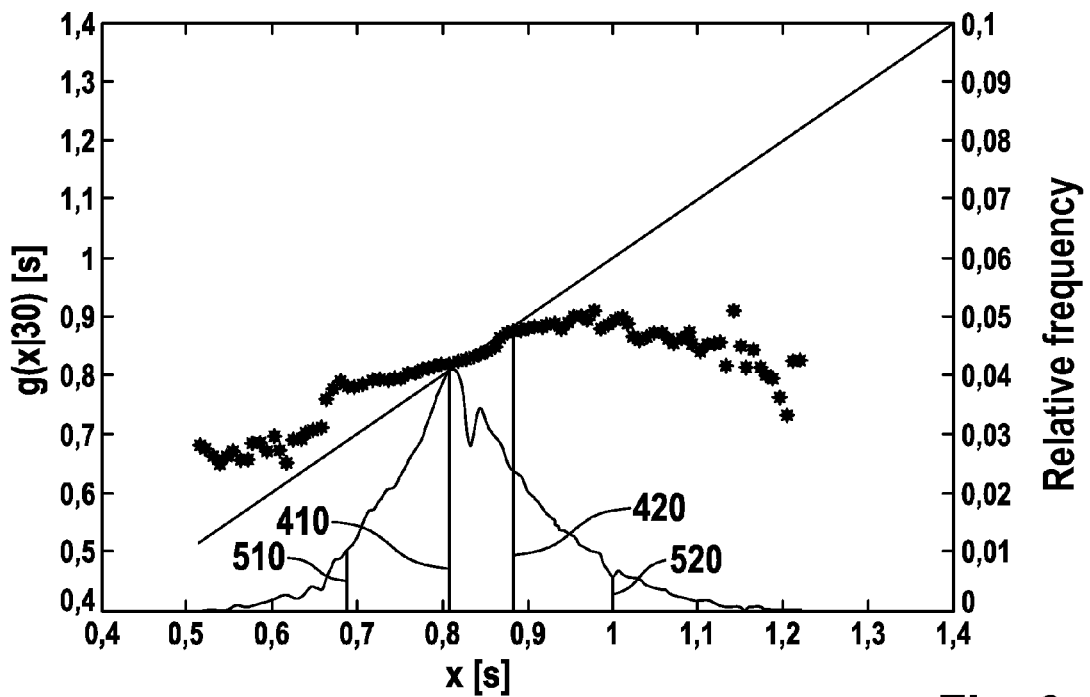
Figure 7:
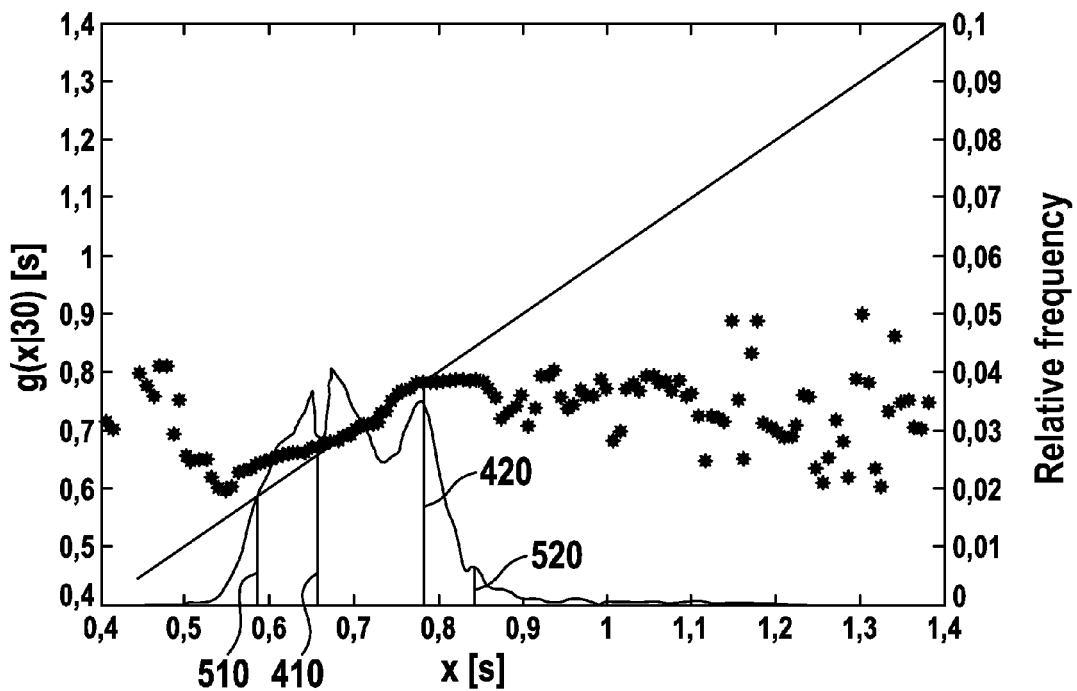
Figure 8:
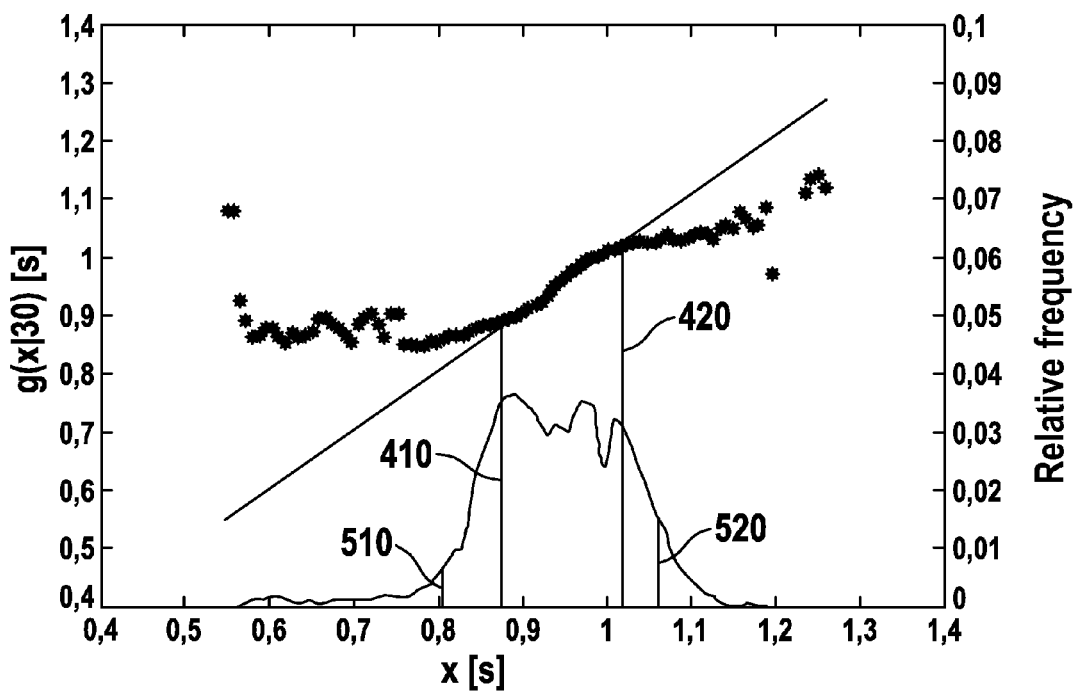

The parameters that are determined on the basis of the plot of g, and their significance within the time series X(t) are shown in FIGS. 3 and 4.

The parameters determined on the basis of the $g(x|\tau)$ plot (FIG. 2) are shown in FIG. 4: Mean heart rates $\xi_1$ and $\xi_2$, which are referred to as the Day Baserate and the Night Baserate, respectively, in FIG. 3 are characterized by vertical lines 410, 420 (these correspond to horizontal lines 310, 320 in FIG. 3). In transition region 430, g follows the straight line having slope 1, as indicated by line 440; at $x = \xi_1$ and $\xi_2$ the data change course and the above-mentioned plateau phases are defined. $\xi_1$ and $\xi_2$ are characterized by vertical lines 410, 420.

The difference between the two baselines ($\xi_2 - \xi_1$) is labeled "Diff". It has the width of transition region 430.

When threshold z is defined, two ranges are defined, which are labeled as Day Area 340, 470 and Night Area 350, 480. In FIG. 3 it is clear that Night Area 350—clearly identified by the elevated RR interval values—is characterized by the fact that most beats are located in Night Area 350.

Derivation of Diagnostically Relevant Statistical Measures

The symbol series S(t) was introduced above as a means for determining the boundaries between diurnal phases and nocturnal phases. In so doing, each individual beat was classified on the basis of one or more threshold values as to whether its value is typical for a sleeping state or a waking state, or possibly for a transition phase.

Statistical parameters that have diagnostic utility can also be derived from S(t). This includes the frequency distribution ranges from 0 to 1 in the entire data series, in one diurnal period or nocturnal period, and/or in windows having a defined length. Secondary parameters can be calculated therefrom, for example, the number of windows having frequency 1 that lies above/below a certain threshold. Moreover, the frequency distributions of the lengths of the subsequences composed of a continuous sequence of just zeroes or ones are of interest.

Measures of this type provide information on the depth of sleep or the waking state, or on the frequency of a sleeping phase/waking phase of a certain depth.

Expansion of the Approach to a Hierarchical-Recursive Method

The method described above is targeted toward the "large structure" of circadian variation, that is, toward the distinction of the characteristics of the diurnal and nocturnal phases. Smaller structures, such as deep-sleep phases, an afternoon nap, or times of particularly high stress, are dominated by the larger structures and are therefore not registered at first.

These smaller structures can likewise be detected by applying the method recursively. That is, the diurnal and nocturnal phases are delineated in a first pass. In the second pass, one of these data segments (or all of them, in parallel) is utilized and is run through the algorithm a second time. For a diurnal phase, the result of this second pass is, for example, the identification of an afternoon nap or a phase of particularly high stress. For a nocturnal phase, it could be possible here to distinguish between different stages of the depth of sleep (light sleep, deep sleep, REM sleep).

Further stages of data processing are feasible, as is the handling of data that are much shorter than 24 hours, although the procedure would be started at a suitable lower level.

According to this expanded method of data processing, in which the steps progress in stages from larger to smaller structures, the delay $\tau$ plays a significant role since it is used to determine the size of the time intervals under examination. Specifically, this means that $\tau$ values between 50 and 5000 beats are well suited for investigating the circadian variation; with smaller structures such as depth of sleep, $\tau$ must be reduced, and so it lies below the typical duration of the phenomena to be investigated.

Given this restriction, for a wide range of $\tau$, the method described herein is stable against variations of $\tau$, that is, the results of a corresponding algorithm show little change within this range (in the case of circadian variation of, for example, 500 to 5000 beats).

Further parameters can be determined using the expanded method, as was described above with regard for the derivation of diagnostic relevant parameters from the investigation of circadian variation. If the investigation is focused, for example, on sleep phases having different levels, the following questions can be answered: What depths of sleep (light, moderate, deep, REM sleep) can be identified? How often, for how long, in what sequence do they each occur? This information therefore also results in indications for the presence of sleep apnea.

Reconstruction of Nighttime Sleeping Behavior

In a further version, the invention will be explained in greater detail by reconstructing nighttime sleeping behavior.

The objective of the following data analysis is to obtain information about a patient's nighttime sleeping behavior based solely on the RR interval time series for the patient. Two types of information can be obtained: the mean heart rate in the sleeping phase and the waking phase; the interval between the two and the absolute values thereof can be an initial indicator of the depth of sleep. In addition, the knowledge of the two mean heart rates makes it possible to define a separating value which can be used to reconstruct the sleeping phase and the waking phase of the particular patient. To validate this approach, in the data records presented below, the reconstructed phases were compared with the classifications that physicians—who were familiar with the data collection—made on the basis of the signals recorded in the sleep laboratory. In addition to the complete ECG, there is also blood pressure, EEG, and breath signal.

The invention was tested on time series of the MIT-BIH Polysomnographic Database from Physionet. The points in time of the R peak in the ECG were used to calculate the RR intervals and the annotations in which the associated sleep phases are assigned in 30 s intervals. The results obtained from four patients, as examples, are presented below.

Calculation and Fit of the Plot of g

The plots of g, which are shown in FIGS. 5 through 8, were calculated for all patients using the following parameter settings:

Delay time $\tau$=30 beats.

Bin width=2/128 Hz=15.625 ms. A bin is defined as the interval of those starting values X(t)=x, the associated successors X(t+$\tau$) of which are averaged in the calculation of $g(x|\tau)=<X(t+\tau)>_{X(t)=x}$, thereby resulting in a point in the plot of g.

The bins overlap each other by one-half of a bin width. Due to the overlap of the bins, each data point contributes to two points on the plot of g.

The plot of g shown in FIGS. 5 through 8 is depicted using asterisks with the value range on the scale on the left; it was fitted using the following piecewise linear function:

$$y_1(x) = \begin{cases} \xi_1 & \text{if } x < \xi_1 \\ x & \text{if } \xi_1 < x < \xi_2 \\ \xi_2 & \text{if } \xi_2 < x \end{cases}$$

Free fit parameters were $\xi_1$ and $\xi_2$ which are depicted in FIGS. 5 through 8 as vertical lines 410, 420. Optimization was carried out using the least squares method, and each g data point was weighted with its relative frequency. FIGS. 5 through 8 also show the line y=x (scale on the left) and the relative frequency of the RR intervals (scale on the right).

In the fit, g values in the lowermost and uppermost 5% quantile were not taken into account. The limits of the disregarded ranges are characterized in the figures using two vertical lines 510, 520.

The results for the four patients are:

Patient 1 (FIG. 5): $\xi_1$=0.87 s $\xi_2$=0.92 s
Patient 2 (FIG. 6): $\xi_1$=0.80 s $\xi_2$=0.88 s
Patient 3 (FIG. 7): $\xi_1$=0.66 s $\xi_2$=0.78 s
Patient 4 (FIG. 8): $\xi_1$=0.88 s $\xi_2$=1.02 s In terms of alternative ways to determine the values by fitting two Gaussian functions to the probability distribution, it becomes clear after examining FIGS. 5 through 8 that this approach is not successful since the distributions are, in individual cases, approximately bimodal, frequently only monomodal, and sometimes even trimodal or multimodal.

Reconstruction of the Sleeping Phases

Based on the $\xi$ values, which were calculated in the previous section, a threshold value z for delineating the sleep phase and the waking phase was defined as the arithmetic mean of the two $\xi$ values:

Patient 1: z=0.88 s
Patient 2: z=0.84 s
Patient 3: z=0.72 s
Patient 4: z=0.95 s

The time series was subdivided into disjoint windows having a width of 90 s. In each of these windows, a test was carried out to determine whether they contain a majority of RR intervals that are greater than or less than z, and were assigned the value S (sleeping) or W (awake) accordingly (see above: description of the classification). Original RR intervals 910, reconstructed sleeping/waking phases 920, and phases 930 according to annotations are shown in FIGS. 9 through 12.

The plot of g presents a way to determine the means of phases of physiologically different conditions, i.e. sleeping phases and waking phases in this case, if their number, temporal location, or associated amplitudes are not known. The knowledge of these means contains information on the depth of sleep and can therefore have diagnostic utility.

Furthermore, the knowledge of these means can be used to define threshold values for delineating sleeping phases and waking phases. The approach is helpful in particular when no additional sensor variables such as activity can be used, because they are either unavailable or too non-specific in the time period under consideration. The threshold values determined in this manner make it possible to delineate the sleeping phases and the waking phases and to therefore quantify the patient's sleeping behavior.

Compared to conventional alternative approaches, the invention has the following advantages:

1. Compared to the use of motion sensors:
   Since the physical activity of a person while sleeping is much lower than it is during the day, sensors of this type are typically inadequate for the purpose of phase delineation. In addition, to obtain the widest possible range of application, it is desirable to use the smallest possible number of required signals. Furthermore, calibration tailored to the patient must be performed when a motion sensor is used since the mass to be moved and the damping properties of the medium in which the implant is enclosed depend on the patient's body weight.

Figure 9:
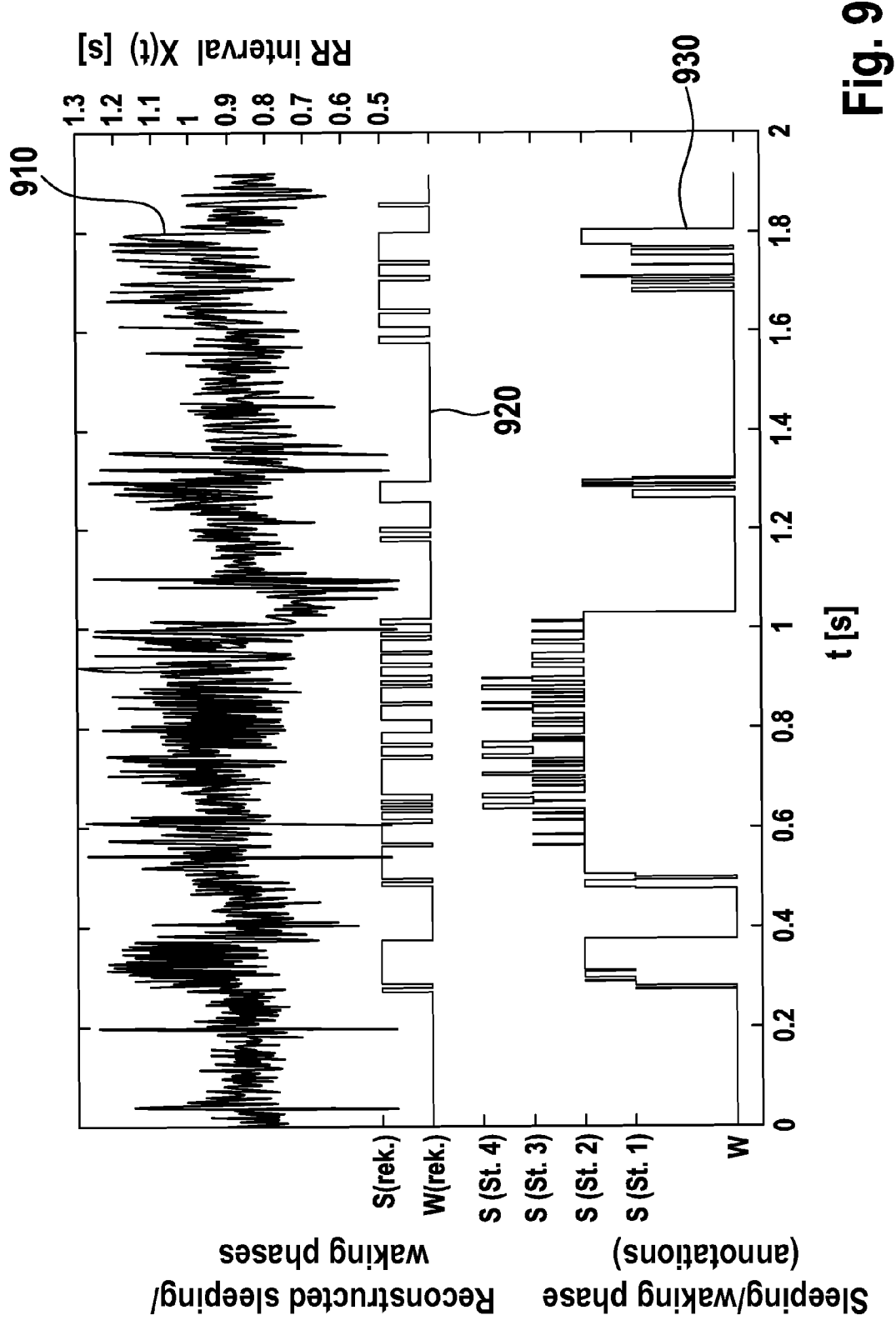
Figure 10:
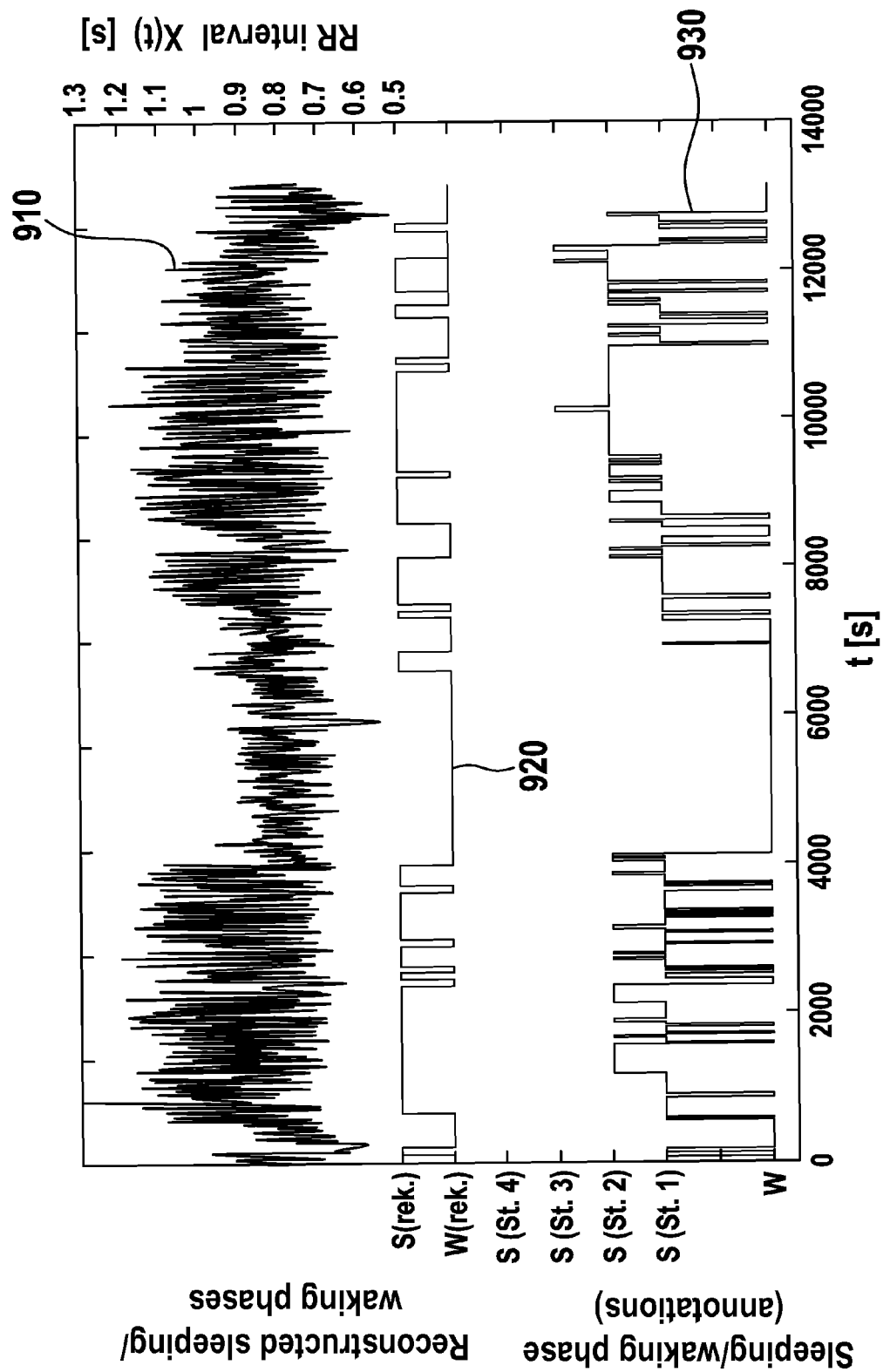
Figure 11:
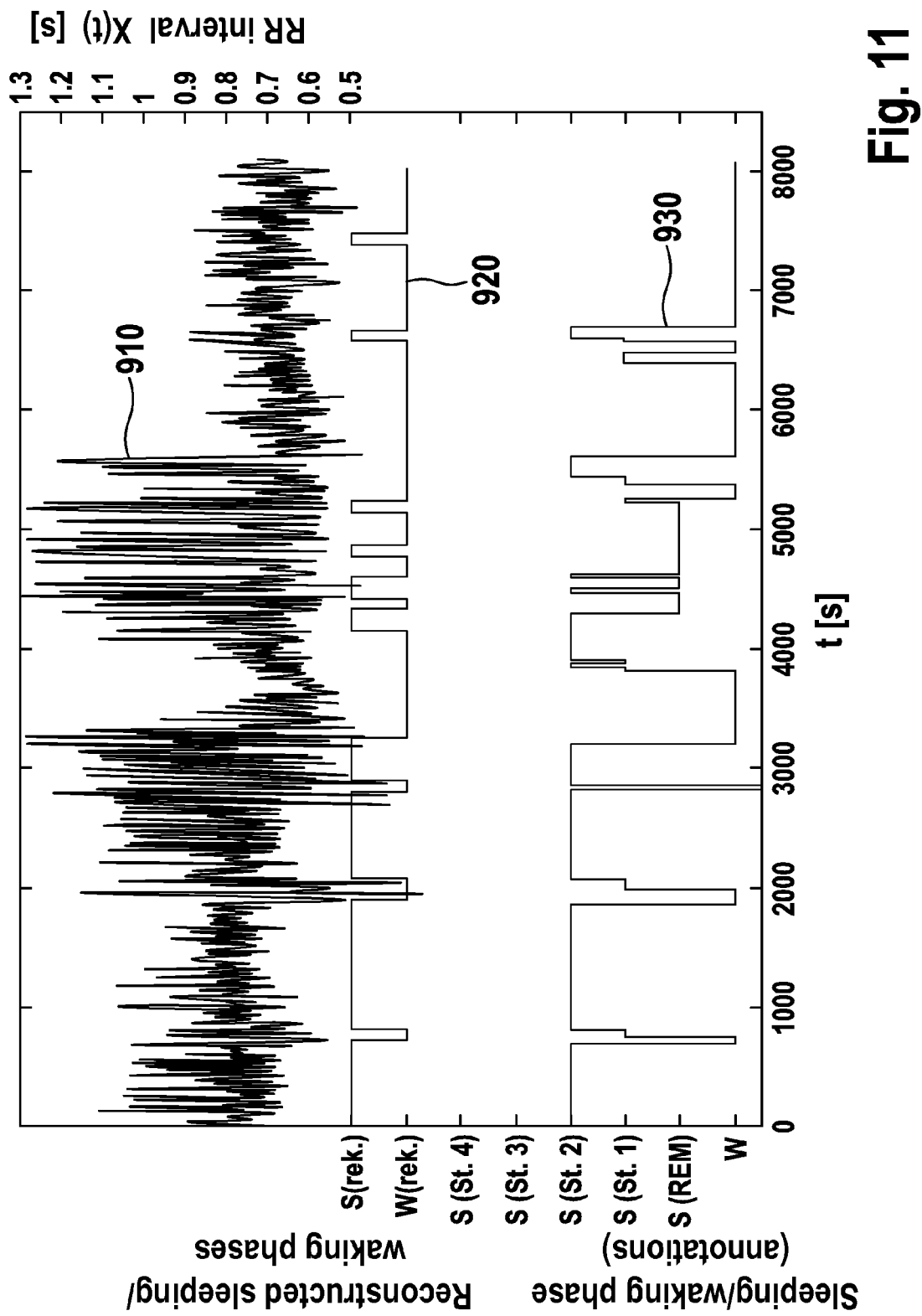
Figure 12:
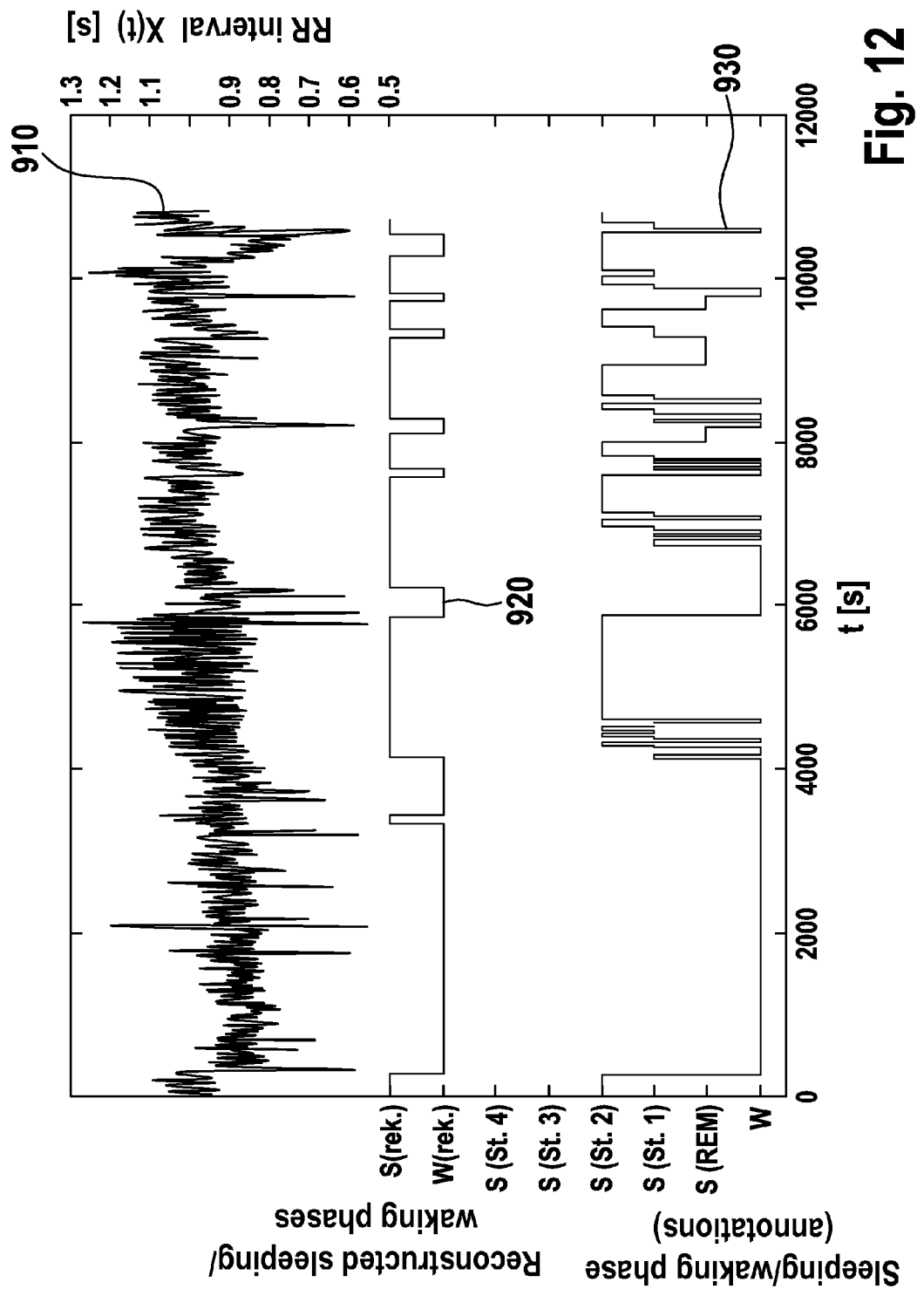

2. Compared to the determination on the basis of the extremes of the time series:
   The time series that are shown illustrate that the extremes, which are the minima in particular in this case, are not representative of sleeping phases and waking phases, and can therefore result in erroneous estimates. To avoid this problem, a good is approach is to first smooth the time series by averaging in a moving window. However, not only do individual beats appear as outliers in the time series, but so do entire time intervals that lie clearly below/above the dominating heart rates. FIG. 9 shows, for example, that there is a distinct break in the RR intervals for a duration of approximately one quarter of an hour. At the same time, however, phases of different depths of sleep having a much smaller width occur. The construction of a suitable algorithm for the smoothing averaging, which eliminates the wide "outlier intervals", but takes them into consideration if they occur sufficiently often, is therefore problematic.

3. Compared to the determination on the basis of the frequency distribution using a fit:

This approach is based on the assumption of a bimodal distribution which is not always given, as shown in FIGS. 5 through 8.

The stated alternative methods according to the prior art therefore show clear potential for misclassifications. In contrast, the inventive method is a stable and simple algorithm that can be used to obtain information about a patient's sleeping behavior.

Proceeding from the time series shown in FIGS. 9 through 12, it becomes clear that different sleeping phases are also reflected in the variance of heart rate. As for RR intervals 910, the inventive method can also be used to determine threshold values therefor, and so supplementing the absolute value criterium with a variance criterium makes it possible to obtain a higher selectivity. But in that case as well, a method is required to define a suitable threshold value, which is accomplished by the invention.

Determination of Mean Diurnal and Nocturnal Heart Rate from 24 h Time Series of RR Intervals The invention includes a method for determining the mean heart rates of two physiologically different states from RR interval time series. Examples of states of this type are daily activity, such as nighttime sleep or rest, physical stress, or sleeping/waking states in the night. The method can be expanded to cover more than two states.

The knowledge of the reconstructed heart rates can be used in two ways: First, they are potential diagnostic markers and/or they make it possible to derive secondary diagnostically relevant parameters. For example, the mean heart rate during the night can be used to delineate healthy subjects from CHF patients with NYHA class I. Second, knowledge of the mean value of the heart rate in each of the two states can be used to delineate the states according to time. For example, day and night can be delineated in the case of 24 h data, sleeping phases and waking phases can be delineated when recordings are made at night, or times of physical stress can be identified. This information can also be used in many ways: Either directly diagnostically (e.g. as a measure of the patient's sleeping behavior), or as a means for data preprocessing, thereby making it possible to use other methods specifically for ranges in exclusively one physiological state.

The inventive method has a number of advantages: It does not require any additional sensor data, in particular no data from motion sensors or similar activity sensors. It does not make any assumptions about the number or temporal location/length of the intervals in which the patient in one of the two states is located. For example, the determination of diurnal heart rate and nocturnal heart rate is insensitive to nocturnal waking phases, afternoon sleep, variable times of falling asleep and waking up, time changes in the summer and winter, or during travel, changes in lifestyle, etc.

The examples presented below are intended to explain in greater detail that the determination of mean heart rates during the day and night based on 24 h data is stable against a non-bimodal frequency distribution, compared to artifacts, and compared to outlier intervals—that is, phenomena that pose risks for alternative methods.

To this end, the data records of the Normal Sinus Rhythm RR Interval Database from PhysioNet were analyzed. Representative examples are presented below.

Plot of g: Calculation of the Plot and the Fit

The plot of g was calculated for all data records using the following parameter settings:

Delay time $\tau$=5000 beats.

Bin width=2/128 Hz=15.625 ms. A bin is defined as the interval of those starting values $X(t)$=x, the associated successors $X(t+'r)$ of which are averaged in the calculation of $g(x|\tau)=<X(t+\tau)>_{X(t)=x}$, thereby resulting in a point in the plot of g.

The bins overlap each other by one-half of a bin width.

The following piecewise linear function was fitted to the plot of g:

$$y_1(x) = \begin{cases} \xi_1 & \text{if } x < \xi_1 \\ x & \text{if } \xi_1 < x < \xi_2 \\ \xi_2 & \text{if } \xi_2 < x \end{cases}$$

Free fit parameters were $\xi_1$ and $\xi_2$, which are depicted as vertical lines 410, 420 in the plot of g in FIGS. 13 through 21. Optimization was carried out using the least squares method, and each g data point was weighted with its relative frequency.

In the fit, g values in the lowermost and uppermost 5% quantile were not taken into account. The limits of the disregarded ranges are characterized in the figures using two vertical lines 510, 520.

Two conventional methods are compared with the invention in the following: Determination of the phase-specific parameters on the basis of the peaks of the frequency distribution of RR intervals 910, or determination of the phase-specific parameters on the basis of extremes in the time series after smoothing. To compare these two methods with the inventive method, the following data are presented in FIGS. 13 through 21:

Panel 1: plot of g (values shown as asterisks, scale on the left) and the line y=x (1310, scale on the left), relative frequency of the RR intervals (1320, scale on the right), and $\xi_1$ and $\xi_2$ (410, 420, as vertical lines)

Panel 2: the time series of RR intervals 910 and $\xi_1$ and $\xi_2$ (310, 320, as horizontal lines)

Panel 3: the time series of RR intervals after smoothing, with window width N=10 beats 1330 and N=300 beats 1340

Panel 4: relative frequency distributions 1350, 1360 of smoothed RR interval time series 1330, 1340

Bimodal Frequency Distribution

Figure 13:
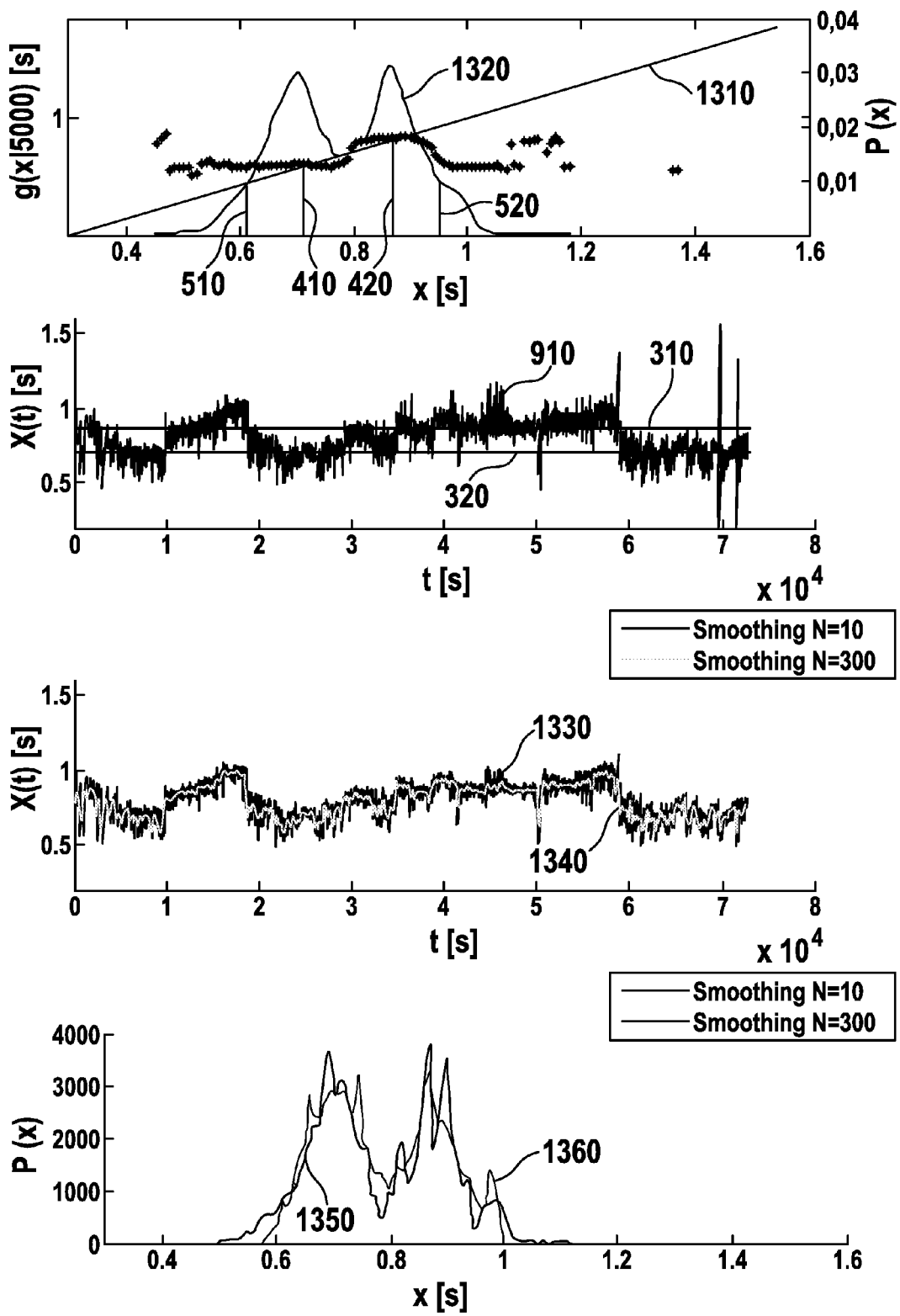
Figure 14:
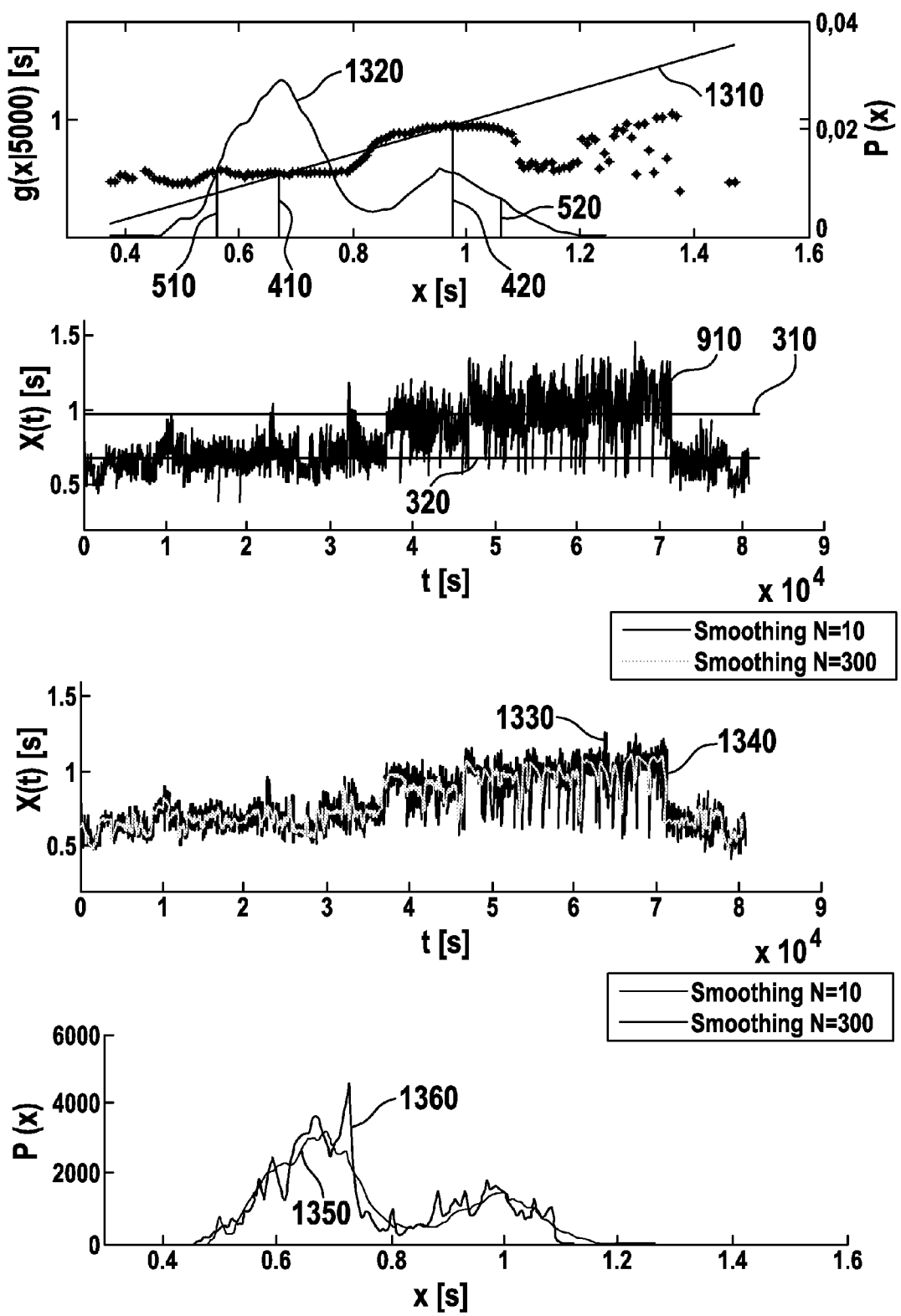

The two examples shown in FIGS. 13 and 14 show the bimodal frequency distribution that is typically assumed for 24 h data, the two modes of which belong to the day and night sections, respectively, of the time series.

The inventive method identifies the two modes that belong to day and night. The three methods that were compared deliver similar results. However, the extreme-value method shown in FIG. 14 slightly underestimates the day mean value by 0.5 s. Histograms 1350, 1360 of the smoothed time series become highly fractured as the size of the window increases.

Monomodal Frequency Distribution

Figure 15:
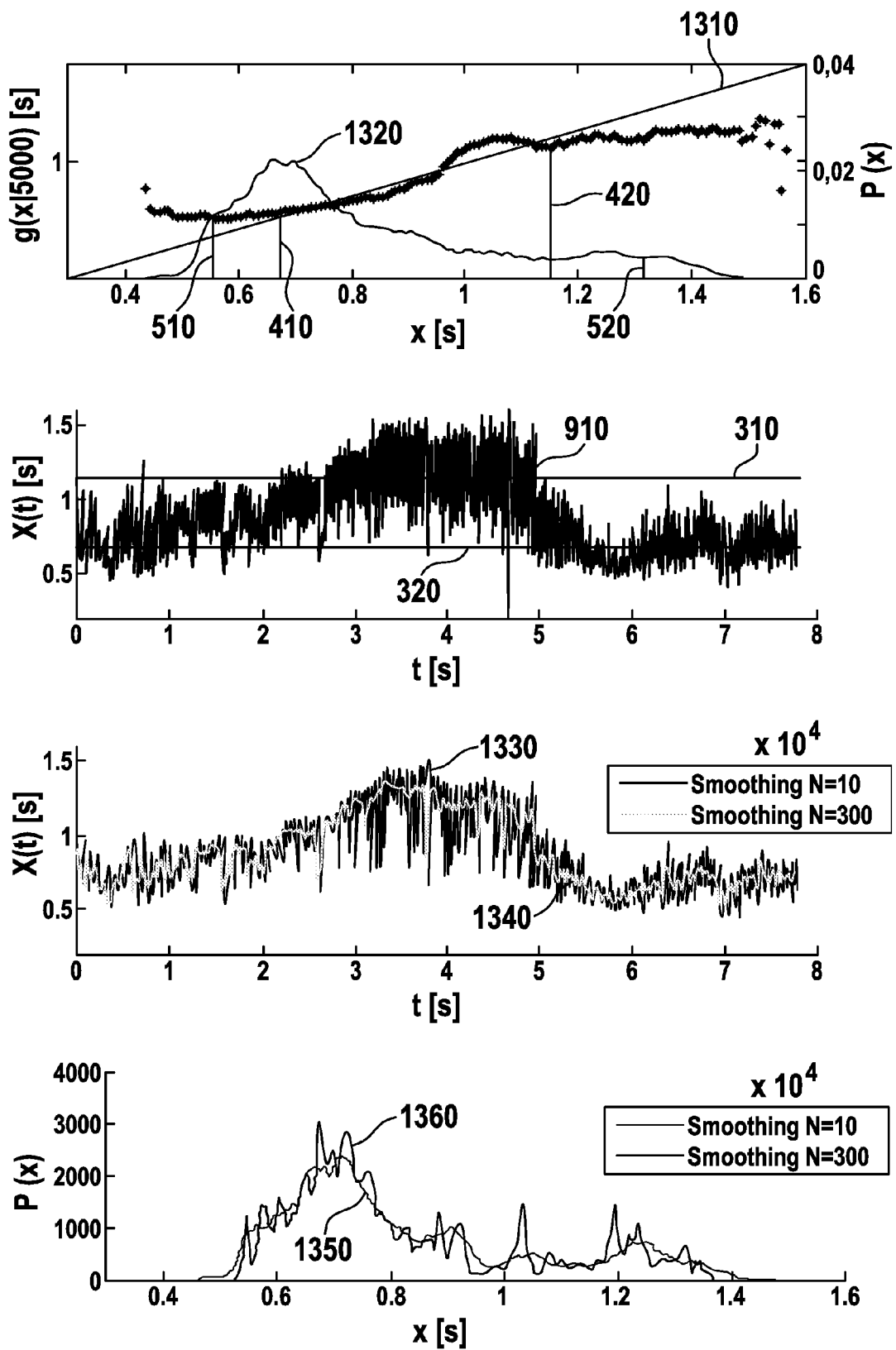
Figure 16:
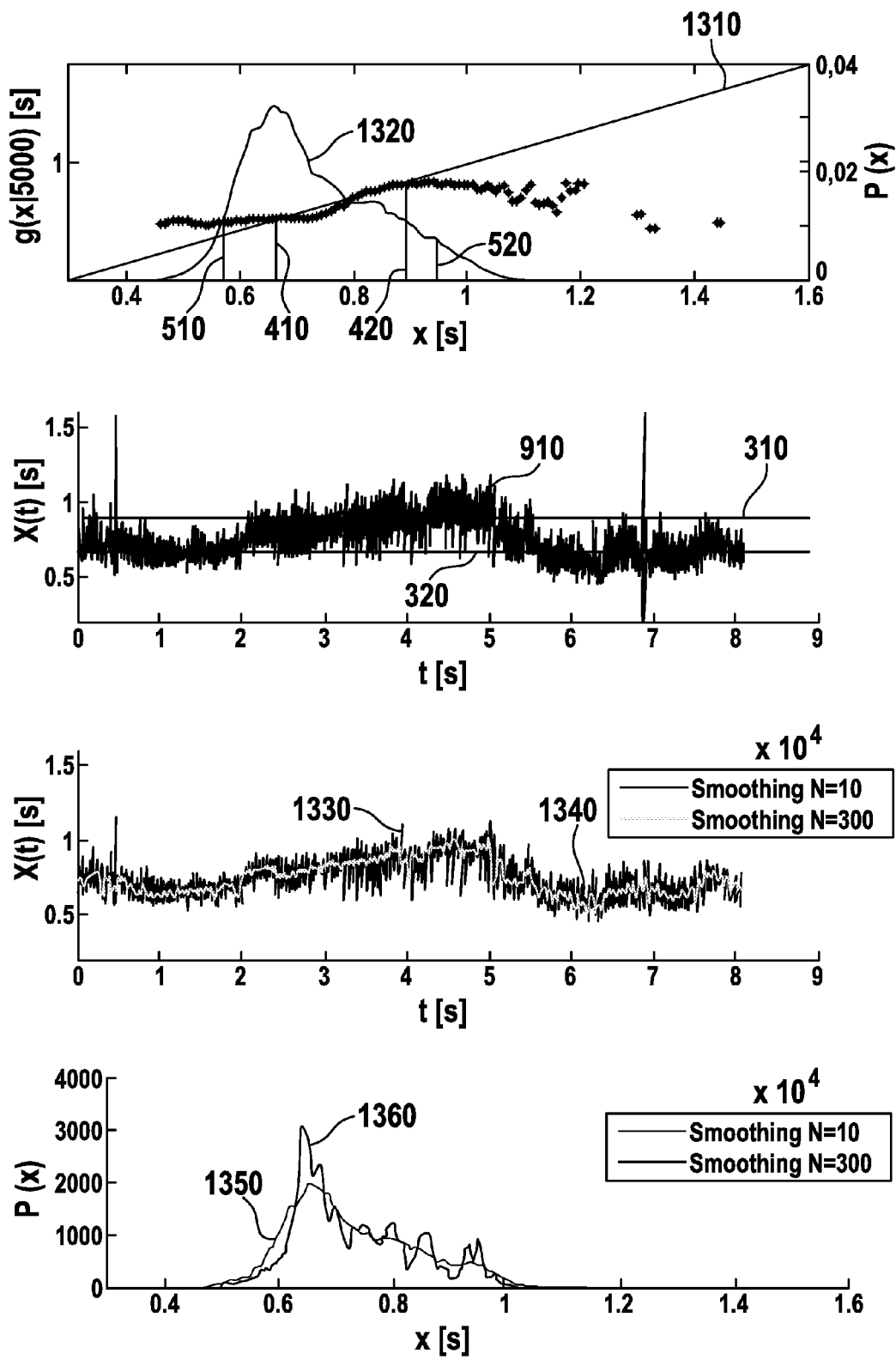

Despite a pronounced circadian variation, the biomodality is very weakly pronounced in the examples shown in FIGS. 15 and 16.

The time series presented here have approximately monomodal frequency distributions. A determination of the nocturnal rate from histograms 1320, 1350, 1360—via detection of local maxima or fitting two Gaussian functions—is very instable and therefore susceptible to error in these cases.

Trimodal and Multimodal Frequency Distribution

Figure 17:
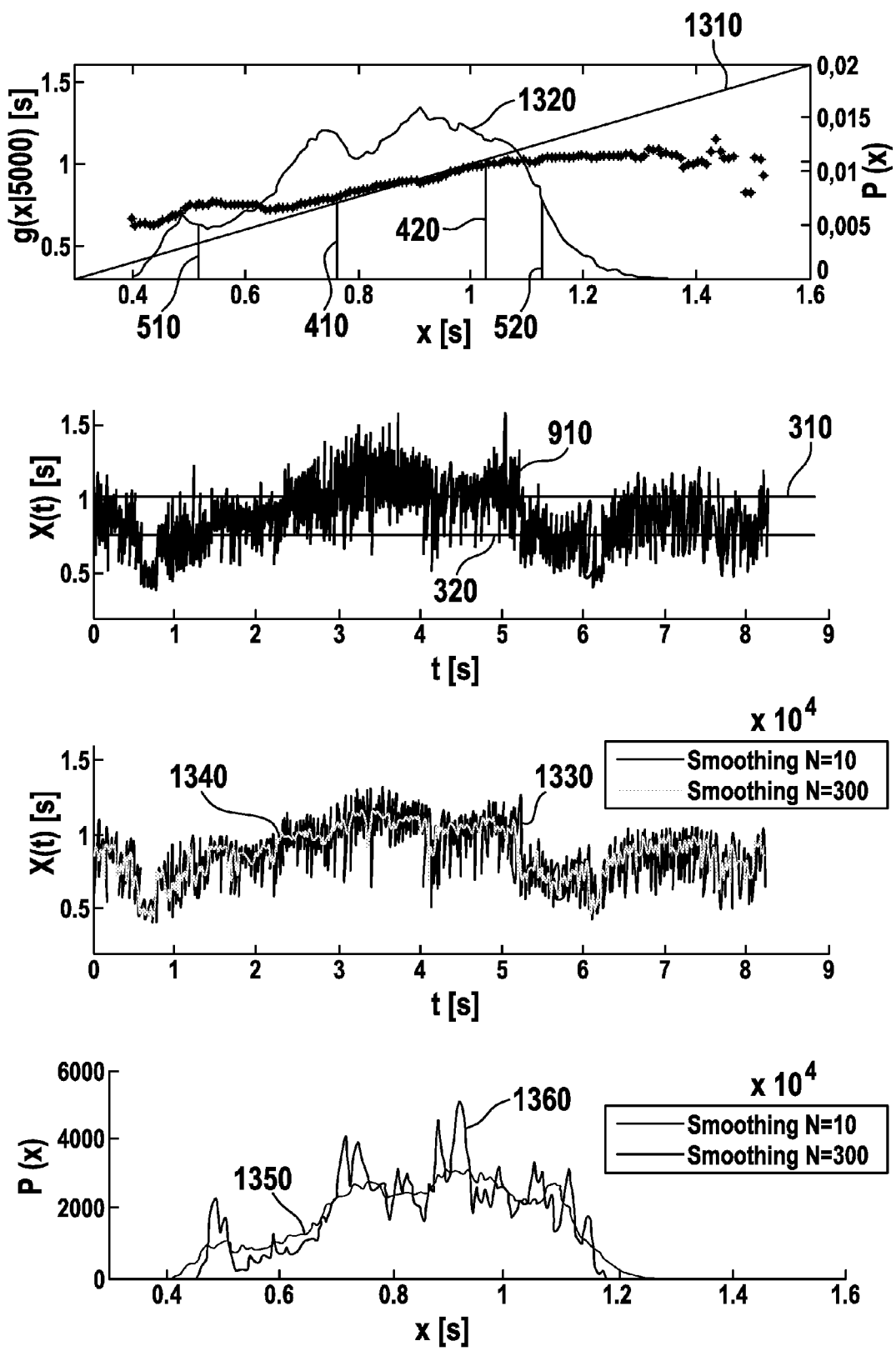
Figure 18:
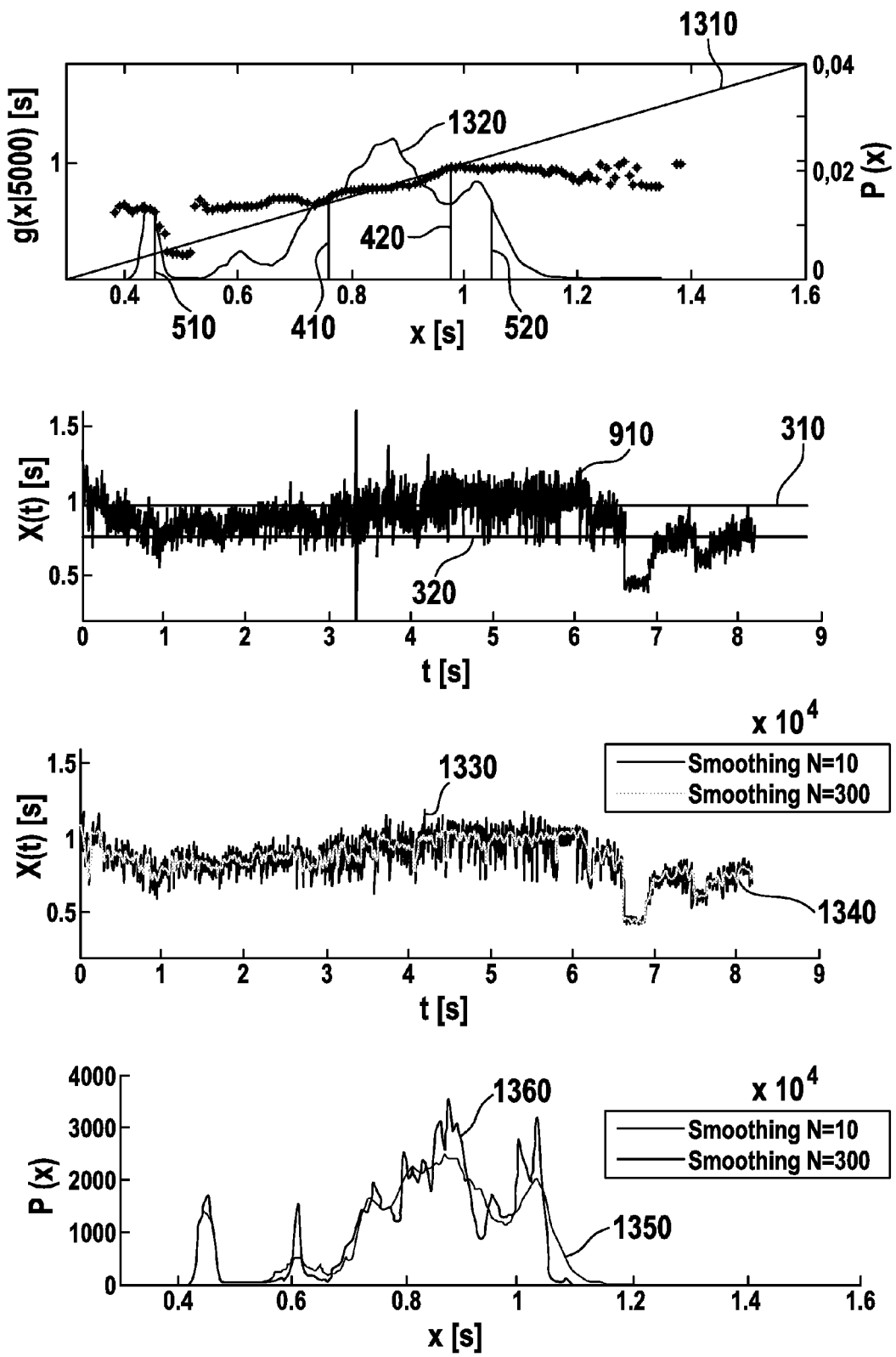

The examples shown in FIGS. 17 and 18 have a clear circadian variation, but they also include phases of particularly high physical activity during the day, which is reflected in the frequency distribution as a trimodality and, in FIG. 18, even as a multimodality.

The examples presented here clearly show the limits of alternative methods based on the determination of extreme values or the fitting of two Gaussian functions in histogram 1320, 1350, 1360. For the latter case, it is shown in FIG. 18 in particular that the most pronounced maximum does not correspond to the diurnal rate or the nocturnal rate; the local maxima in histogram 1320, 1350, 1360 therefore do not necessarily correspond to the values for $\xi_1$ and $\xi_2$ being sought. Even if this were the case, selecting the correct maxima becomes somewhat problematic: The fitting of two Gaussian functions becomes unstable; the optimization will cover the majority of the distribution using a single Gaussian fit and practically randomly place the remainder, and/or place the two Gaussian functions using the greatest possible distance, to cover the histogram to the greatest extent possible.

If a fit is not performed, additional criteria become necessary for selecting the two local maxima that are used. In each case, the methods, which determine $\xi_1$ and $\xi_2$ from one of the histograms 1320, 1350, 1360, would require correction steps which make the method more complicated.

Smoothing the data—as proposed—does not help either. An improvement in histograms 1350, 1360 in the direction toward a more pronounced bimodality is not observed. Furthermore, the extreme value method is not successful either, since phases of high physical activity for more than approximately one hour, as can be seen with subject 6 (FIG. 18), are nearly impossible to eliminate via averaging even when very long moving windows are used. They result in a clear underestimation of the mean diurnal RR interval and therefore corrupt, for example, characteristic values that use the interval between diurnal heart rate and nocturnal heart rate for diagnostic purposes.

Artifacts

Figure 19:
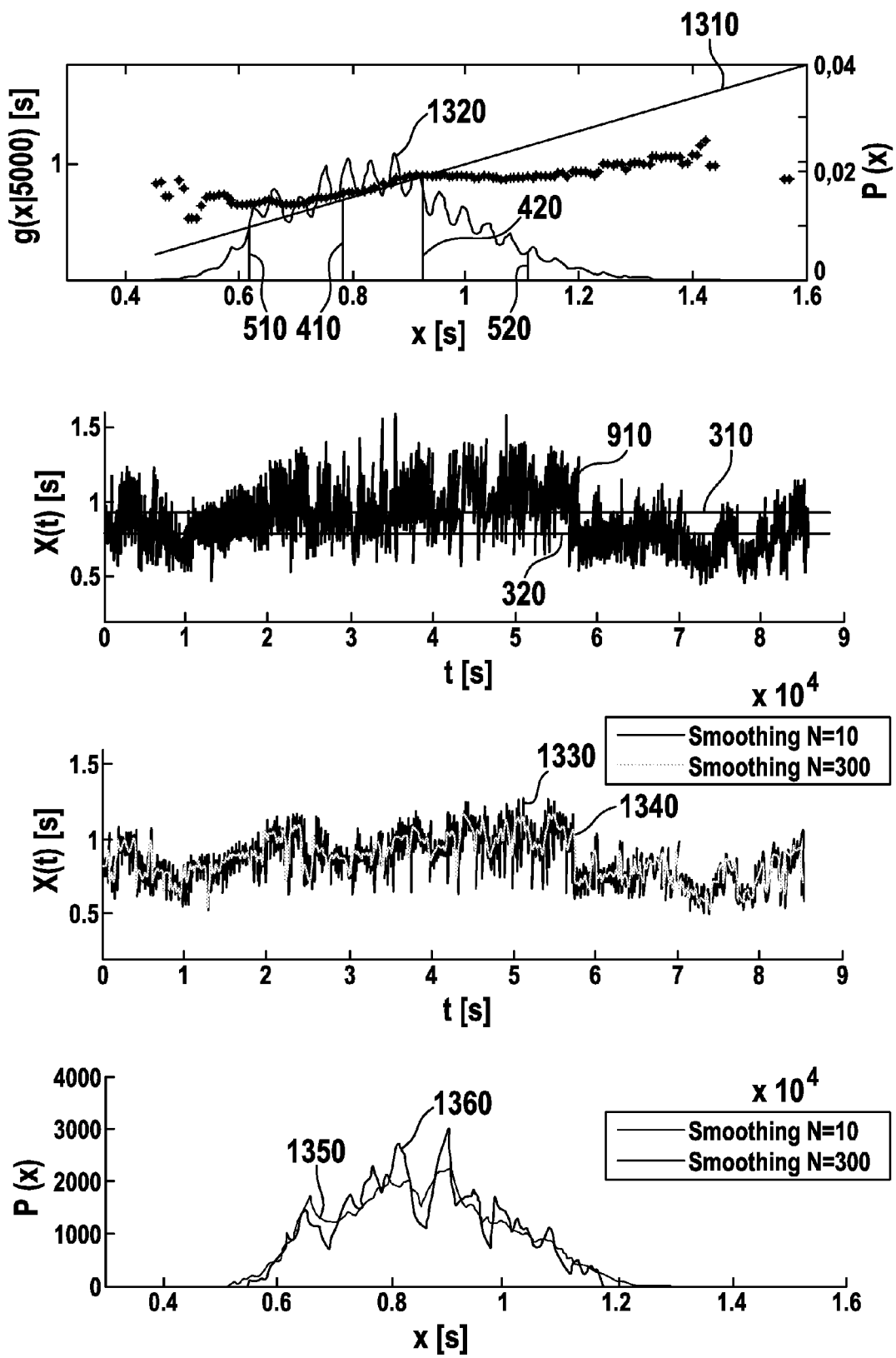
Figure 20:
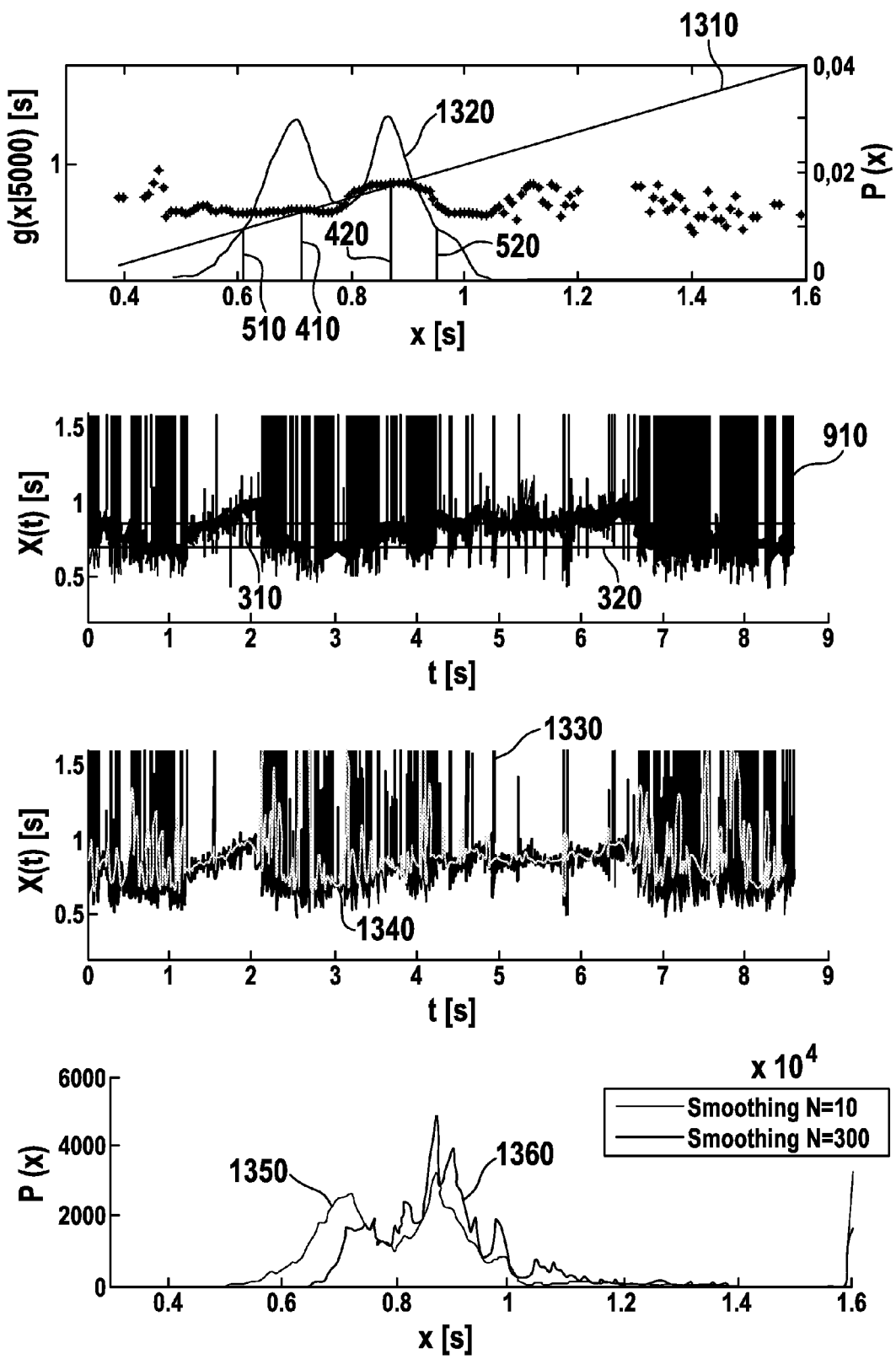
Figure 21:
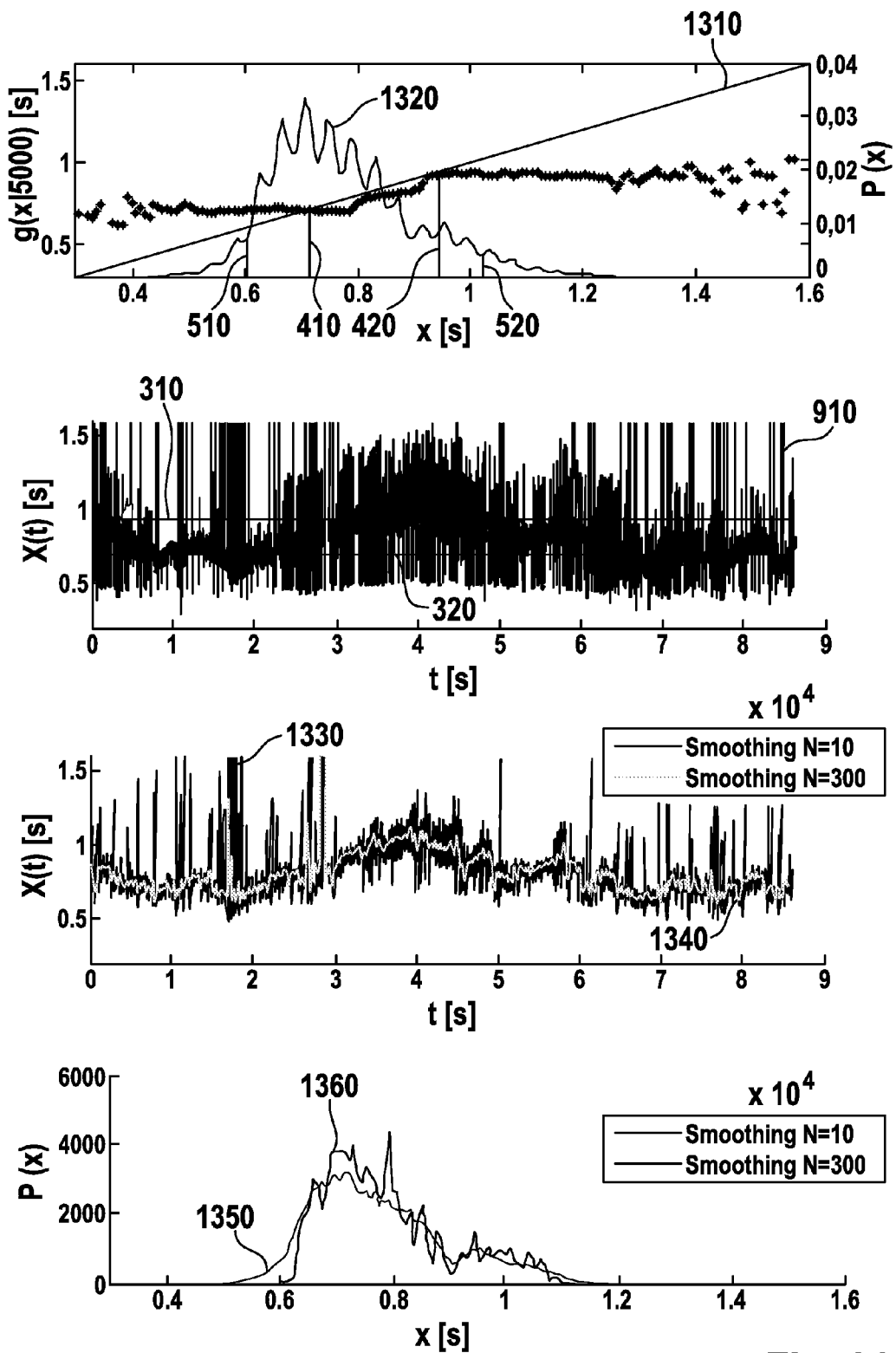

The examples presented in FIGS. 19 through 21 demonstrate that the inventive method delivers suitable results even when the frequency distribution has distinct ripples, or when the time series contains several artifacts or extra systoles. (FIG. 20 presents the data that were also used in FIG. 13, although they are unfiltered in FIG. 20).

FIGS. 13 through 21 show that the inventive method is stable to deviations from properties that are typically expected of 24 h RR interval time series, i.e. against non-bimodal (mono-, tri- and multimodal) frequency distributions, against phases that deviate from the circadian course (ranges of high physical activity), and against a high number of artifacts or extra systoles. In all of these cases, the inventive method delivers results that can be classified as being correct when examined via inspection on the basis of the time series.

According to a conventional method, mean heart rates are determined from the frequency distribution of the RR intervals, for example, by fitting two Gaussian functions or identifying the two local maxima. In the case of the monomodal and polymodal distributions in particular, this shows a high risk for unstable behavior and misclassifications.

The comparison with smoothed data showed that even this conventional method has distinct disadvantages. As a result, greater bimodality could not be achieved in the probability distributions; instead, histograms 1350, 1360 were fractured to a greater extent.

Likewise, smoothing did not provide protection against misclassifications if the diurnal and nocturnal heart rates were identified using the extremes of the time series.

Moreover, it was demonstrated that the plot-of-g method is stable against artifacts and extra systoles which occur frequently in cardiological time series.

The method, according to the invention, using calculation and fitting of the plot of g is therefore a simple method in the case of 24 h data, which functions with few assumptions and parameters and, primarily, is stable against atypical behavior of the time series. These properties are important for a method that should be used to process unknown data. In particular, when processing is performed in an implant, it is unrealistic to intervene in the method or perform calibration. Stability is therefore a prerequisite that cannot be underestimated.

The invention, in its version, is not limited to the preferred versions described above. Instead, a number of variants are feasible which utilize the system according to the invention and the inventive method, even in fundamentally different versions.

It will be apparent to those skilled in the art that numerous modifications and variations of the described examples and versions are possible in light of the above teaching. The disclosed examples and versions are presented for purposes of illustration only. Therefore, it is the intent to cover all such modifications and alternate versions as may come within the scope of the claims below, or which are legally equivalent to the matter therein.

What is claimed is:

1. A method for adapting treatment delivered by a medical device to a body, the method including the steps of:
   a. determining phase-specific parameters of a measured physiological variable X(t), each phase-specific parameter being defined by a mean $g(x|\tau)$ for at least some values x of X(t) within a specified time period, the mean $g(x|\tau)$ being calculated for each of the values X(t+$\tau$), the predecessors X(t) of which had the value x, wherein $\tau$ defines a time interval; and
   b. delivering treatment to the body at least partially in dependence on the determined phase-specific parameters;
   wherein the step of determining phase specific parameters includes determining at least one of:
   i. a phase specific mean $\xi$ of the variable X(t), and
   ii. boundaries between different phases of the variable X(t).

2. The method of claim 1 wherein the medical device includes one or more of:
   a. a cardiac pacemaker,
   b. a defibrillator, and
   c. a patient monitoring device.

3. The method of claim 1 wherein the variable X(t) is one of:
   a. heart rate,
   b. respiration, or
   c. chemical and/or biochemical signals.

4. The method of claim 1 wherein the phase-specific parameters are defined solely by the mean $g(x|\tau)$.

5. The method of claim 1 wherein the phase-specific parameters are defined by:
   a. the mean $g(x|\tau)$, and
   b. X(t) and/or further measured variables.

6. The method of claim 1 wherein the step of determining phase-specific parameters includes determining the length of a phase of the variable X(t).

7. The method of claim 6 wherein the length of the phase of the variable X(t) is defined by the time period of the phase.

8. The method of claim 1 wherein the boundaries of a phase of the variable X(t) are determined in dependence on at least one phase-specific mean $\xi$.

9. The method of claim 1 further including the step of classifying the variable X(t) by assigning values of X(t) to a phase identified within the variable X(t).

10. The method of claim 1 wherein the step of determining phase-specific parameters includes recursively calculating the function $g(x|\tau)$.

11. The method of claim 1 further including the step of downloading instructions from an electronic data network onto a data processing device, wherein execution of the instructions by the data processing device implements the method of claim 1.

12. A non-transitory, machine-readable storage medium bearing encoded instructions, wherein execution of the instructions implements the method of claim 1.

13. A method for adapting treatment delivered by a medical device to a body, the method including the steps of:
   a. determining phase-specific parameters of a measured physiological variable X(t), each phase-specific parameter being defined by a mean $g(x|\tau)$ for at least some values x of X(t) within a specified time period, the mean $g(x|\tau)$ being calculated for each of the values X(t+$\tau$), the predecessors X(t) of which had the value x, wherein $\tau$ defines a time interval;
   b. delivering treatment to the body at least partially in dependence on the determined phase-specific parameters; and
   c. classifying the variable X(t) by assigning values of X(t) to a phase identified within the variable X(t);
   wherein one or more of:
   i. the boundaries of the phase of the variable X(t), and/or
   ii. the length of the phase of the variable X(t),
   are determined by evaluating at least some of the classified values of the variable X(t).

14. A method for adapting treatment delivered by a medical device to a body, the method including the steps of:
   a. determining phase-specific parameters of a measured physiological variable X(t), each phase-specific parameter being defined by a mean $g(x|\tau)$ for at least some values x of X(t) within a specified time period, the mean $g(x|\tau)$ being calculated for each of the values X(t+$\tau$), the predecessors X(t) of which had the value x, wherein $\tau$ defines a time interval; and
   b. delivering treatment to the body at least partially in dependence on the determined phase-specific parameters;
   wherein:
   i. the mean $g(x|\tau)$ is approximated by function y(x), and
   ii. the phase-specific parameters are determined by evaluating the function y(x).

15. The method of claim 14 wherein the function y(x) is a piecewise linear function $y_l(x)$.

16. The method of claim 14 wherein the function y(x) is a sigmoidal function $y_s(x)$.

17. A medical device configured to:
   a. determine phase-specific parameters of a physiological variable X(t) measured from a body, each phase-specific parameter being defined by a mean $g(x|\tau)$ for at least some values x of X(t) within a specified time period, the mean $g(x|\tau)$ being calculated for each of the values X(t+$\tau$), the predecessors X(t) of which had the value x, wherein $\tau$ defines a time interval; and
   b. define a treatment to be delivered to the body at least partially in dependence on the determined phase-specific parameters;
   wherein determining phase specific parameters includes determining at least one of:
   i. a phase specific mean $\xi$ of the variable X(t), and
   ii. boundaries between different phases of the variable X(t).

18. The medical device of claim 17 wherein the medical device includes one or more of:
   a. a cardiac pacemaker,
   b. a defibrillator, and
   c. a patient monitoring device.

19. The medical device of claim 17 including a processor, wherein the processor has a computer program loaded therein which configures the processor to determine the phase-specific parameters of the physiological variable X(t).

* * * * *